United States Patent
Zhong

(10) Patent No.: US 12,228,405 B2
(45) Date of Patent: Feb. 18, 2025

(54) METHOD FOR MEASURING HEIGHT ON PLANE AND DEVICE

(71) Applicant: Huawei Technologies Co., Ltd., Shenzhen (CN)

(72) Inventor: Zhen Zhong, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 353 days.

(21) Appl. No.: 17/762,579

(22) PCT Filed: Aug. 25, 2020

(86) PCT No.: PCT/CN2020/111077
§ 371 (c)(1),
(2) Date: Mar. 22, 2022

(87) PCT Pub. No.: WO2021/057361
PCT Pub. Date: Apr. 1, 2021

(65) Prior Publication Data
US 2022/0342088 A1    Oct. 27, 2022

(30) Foreign Application Priority Data

Sep. 24, 2019   (CN) .......................... 201910905161.8

(51) Int. Cl.
*G01C 21/00*     (2006.01)
*G01C 5/00*      (2006.01)
(Continued)

(52) U.S. Cl.
CPC .......... *G01C 21/005* (2013.01); *G01C 5/005* (2013.01); *G01C 5/06* (2013.01); *G01C 23/00* (2013.01);
(Continued)

(58) Field of Classification Search
CPC .. A61B 5/681; A63B 2220/73; G01C 21/005; G01C 23/00; G01C 5/005; G01C 5/06; G01S 19/34; G01S 19/39; G01S 19/53
See application file for complete search history.

(56) References Cited

U.S. PATENT DOCUMENTS 6,970,795 B1 *  11/2005  Burgett ................... G01S 19/42
                                                  702/85
2002/0126041 A1 *  9/2002  Hedrick ................. G01C 5/005
                                                  342/120
(Continued)

FOREIGN PATENT DOCUMENTS

CN        103713305 A    4/2014
CN        103728644 A    4/2014
(Continued)

OTHER PUBLICATIONS

Lin et al, Electronic Barometric Altimeter in Real Time Correction, IEEE, 2008 (Year: 2008).*

(Continued)

*Primary Examiner* — David L Singer
(74) *Attorney, Agent, or Firm* — Conley Rose, P.C.

(57) ABSTRACT

A method for measuring a height on a plane, implemented by an electronic device, includes displaying an altitude obtained in a first detection manner, and displaying an altitude obtained in a second detection manner when a first switching condition is met. In this way, the electronic device displays an altitude detected based on a barometric pressure sensor. When a barometric pressure value of an environment in which the electronic device is located is inconsistent with an atmospheric pressure value, the data of the barometric pressure sensor is invalid. The electronic device displays an altitude obtained in another detection manner. In this way, (Continued)

the electronic device can display an accurate altitude in a case in which a user takes a plane.

20 Claims, 17 Drawing Sheets

(51) Int. Cl.
*G01C 5/06* (2006.01)
*G01C 23/00* (2006.01)
*G01S 19/53* (2010.01)
*A61B 5/00* (2006.01)
*G01S 19/34* (2010.01)

(52) U.S. Cl.
CPC .......... *A61B 5/681* (2013.01); *A63B 2220/73* (2013.01); *G01S 19/34* (2013.01); *G01S 19/53* (2013.01)

(56) References Cited

U.S. PATENT DOCUMENTS

| | | | | |
|---|---|---|---|---|
| 2007/0068245 | A1* | 3/2007 | Blondeau | G04G 21/02 73/179 |
| 2012/0072110 | A1* | 3/2012 | Venkatraman | G01C 21/08 701/434 |
| 2013/0257650 | A1 | 10/2013 | Miyake | |
| 2014/0135040 | A1* | 5/2014 | Edge | G01C 5/06 455/456.6 |
| 2014/0278220 | A1 | 9/2014 | Yuen | |
| 2015/0042516 | A1* | 2/2015 | Cui | G01S 1/02 342/450 |
| 2015/0054664 | A1* | 2/2015 | Dupont De Dinechin | G01C 23/00 340/973 |
| 2015/0247917 | A1* | 9/2015 | Gum | H04W 4/029 342/462 |
| 2017/0205232 | A1* | 7/2017 | Shirai | G01S 19/42 |
| 2017/0277129 | A1 | 9/2017 | Iijima et al. | |
| 2018/0364065 | A1 | 12/2018 | Toda | |
| 2021/0027637 | A1* | 1/2021 | Cazaux | G08G 5/045 |

FOREIGN PATENT DOCUMENTS

| | | |
|---|---|---|
| CN | 104208865 A | 12/2014 |
| CN | 106153001 A | 11/2016 |
| CN | 205785183 U | 12/2016 |
| CN | 106595577 A | 4/2017 |
| CN | 106772496 A | 5/2017 |
| CN | 206728014 U | 12/2017 |
| CN | 108072356 A | 5/2018 |
| CN | 109141348 A | 1/2019 |
| CN | 109282786 A | 1/2019 |
| JP | 2018036223 A | 3/2018 |
| WO | 0210680 A2 | 2/2002 |
| WO | 2012037470 A1 | 3/2012 |

OTHER PUBLICATIONS

Parviainen et al, Differential Barometry in Personal Navigation, IEEE, 2008 (Year: 2008).*

Brzozowski et al, Measurement data fusion in the display system for hang-glider and paraglider, IEEE, 2017 (Year: 2007).*

Li et al, Using Barometers to Determine the Height for Indoor Positioning, 2013 International Conference on Indoor Positioning and Indoor Navigation, Oct. 28-31, 2013 (Year: 2013).*

Donna Roberts, Error in Measurement, MathBitsNotebook, Retrieved from the Internet: <URL: https://web.archive.org/web/20190107211211/ https://mathbitsnotebook.com/Algebra1/Units/UNError.html> (Year: 2019).*

Baidu Encyclopedia, "pressure up formula," 2007, 6 pages.

Baidu Encyclopedia, "aircraft cockpit pressurization," 2017, 4 pages.

Wikipedia, "Barometric formula," 2016, 5 pages.

* cited by examiner

METHOD FOR MEASURING HEIGHT ON PLANE AND DEVICE

CROSS-REFERENCE TO RELATED APPLICATIONS

This is a U.S. National Stage of International Patent Application No. PCT/CN2020/111077 filed on Aug. 25, 2020, which claims priority to Chinese Patent Application No. 201910905161.8 filed on Sep. 24, 2019, both of which are hereby incorporated by reference in their entireties.

TECHNICAL FIELD

This application relates to the field of terminal technologies, and in particular, to a method for measuring a height on a plane and a device.

BACKGROUND

Many wearable devices such as various sports watch products have an "altimeter" function, in other words, current altitudes of the devices can be displayed on the devices. As shown in FIG. 1, a smart watch has an "altimeter" function, and displays a current altitude 121 meters of the smart watch.

Generally, the wearable devices implement the "altimeter" function by using barometric pressure sensors. Atmospheric pressure changes with an altitude. A barometric formula describes how atmospheric pressure changes with an altitude. The wearable device may calculate a current altitude based on a barometric pressure value measured by the barometric pressure sensor and the barometric formula.

However, in some cases, barometric pressure of an environment in which the wearable device is located is not atmospheric pressure. For example, when a user takes a plane with a wearable device, because pressure is boosted in a cabin of the plane, a barometric pressure value measured by a barometric pressure sensor is not an atmospheric pressure value corresponding to a current altitude. A height value calculated by the wearable device based on the barometric pressure value measured by the barometric pressure sensor and the barometric formula is not a true altitude of the wearable device. In other words, in this case, the data of the barometric pressure sensor of the wearable device is untrustworthy, and an "altimeter" function of the wearable device fails. For example, when a user takes a plane with a smart watch, the plane has flown nearly 10 thousand meters high, while an altitude displayed on the smart watch is only approximately 2000 meters.

SUMMARY

Embodiments of this application provide a method for measuring a height on a plane and a device, so that an electronic device such as a wearable device can display an accurate altitude when data of a barometric pressure sensor is untrustworthy in a case in which a user takes a plane or in another case.

According to a first aspect, an embodiment of this application provides a method for measuring a height on a plane. The method may include: An electronic device displays an altitude obtained in a first detection manner: and if it is determined that a first switching condition is met, the electronic device displays an altitude obtained in a second detection manner.

In the method, the electronic device may switch, based on a condition such as an environment in which the electronic device is located, a detection manner of obtaining an altitude. In this case, when a detection manner is invalid, the electronic device may switch to another detection manner, so that the electronic device displays an accurate altitude.

In a possible design, the first switching condition includes: the data obtained by the electronic device in the first detection manner is invalid. In other words, when the first detection manner is invalid, the altitude obtained in the first detection manner is inaccurate, and the electronic device switches from displaying the altitude obtained in the first detection manner to displaying the altitude obtained in the second detection manner, to display an accurate altitude.

In a possible design, if the electronic device determines that a value by which an altitude value of the electronic device increases within first preset duration is greater than a preset first height threshold, the electronic device determines that the data obtained in the first detection manner is invalid.

In this manner, if the electronic device determines that the value by which the altitude value of the electronic device increases within the first preset duration is greater than the preset first height threshold, the electronic device may determine that a plane that a user takes with the electronic device takes off. After the plane takes off, pressure is boosted in a cabin of the plane, and in this case, the data obtained in the first detection manner is invalid.

In a possible design, if the electronic device determines, when displaying the altitude obtained in the second detection manner, that a second switching condition is met, the electronic device displays the altitude obtained in the first detection manner.

In the method, the electronic device may switch, based on the condition such as the environment in which the electronic device is located, back to displaying the altitude obtained in the first detection manner.

In a possible design, the second switching condition includes: the data obtained by the electronic device in the first detection manner becomes valid again. In other words, when the first detection manner becomes valid again, the altitude obtained in the first detection manner is accurate, and the electronic device switches from displaying the altitude obtained in the second detection manner to displaying the altitude obtained in the first detection manner. In some scenarios, for example, if the altitude obtained in the first detection manner is more accurate, switching, by the electronic device in a timely manner, back to displaying the altitude obtained in the first detection manner can enable an altitude value displayed by the electronic device to be more accurate. For example, if the second detection manner is relatively power-consuming, switching, by the electronic device in a timely manner, back to displaying the altitude obtained in the first detection manner can reduce power consumption.

In a possible design, if the electronic device determines that an absolute value of a difference between the altitude obtained in the first detection manner and the altitude obtained in the second detection manner is less than a preset threshold, it indicates that the altitude obtained in the first detection manner is accurate, and the electronic device may determine that the data obtained in the first detection manner becomes valid again.

In a possible design, if the electronic device determines that a value by which the altitude value of the electronic device decreases within second preset duration is greater than a preset second height threshold, it indicates that the plane that the user takes with the electronic device lands, and the electronic device may determine that the data obtained in the first detection manner becomes valid again.

In a possible design, the second switching condition includes: the electronic device detects an operation of disabling the second detection manner by the user. If the user disables the second detection manner, the electronic device cannot obtain the altitude in the second detection manner, and the electronic device switches from displaying the altitude obtained in the second detection manner to displaying the altitude obtained in the first detection manner.

In a possible design, the first detection manner is detecting the altitude of the electronic device by using a barometric pressure sensor, and the second detection manner is receiving altitude data in data of a GNSS and obtaining the altitude of the electronic device.

In a possible design, before displaying the altitude obtained in the second detection manner, the electronic device enables a GNSS function of the electronic device. The electronic device can receive the altitude data in the data of the GNSS only when the GNSS function is enabled, to obtain the altitude of the electronic device and display the altitude.

In a possible design, the electronic device periodically enables the GNSS function of the electronic device based on a preset first time interval. Because power consumption of the GNSS function is relatively large, periodically enabling the GNSS function based on the time interval can reduce power consumption compared with a case in which the GNSS function is always enabled.

According to a second aspect, an embodiment of this application provides an electronic device. The electronic device may implement the method for measuring a height on a plane according to the first aspect. The electronic device may implement the foregoing method by using software or hardware or by using hardware executing corresponding software.

In a possible design, the electronic device may include a display, a processor, and a memory. The display and the processor are configured to support the electronic device in performing a corresponding function in the method in the first aspect. The memory is configured to be coupled to the processor, and store program instructions and data that are necessary for the electronic device. In addition, the electronic device may further include a communications interface, configured to support communication between the electronic device and another electronic device. The communications interface may be a transceiver or a transceiver circuit.

In a possible design, the electronic device may include a processing module, a display module, a first detection module, and a second detection module. The display module is configured to display an altitude obtained by the first detection module, and is further configured to display an altitude obtained by the second detection module. The processing module is configured to: determine whether a first switching condition is met; and if it is determined that the first switching condition is met, determine that the display module is to display the altitude obtained by the second detection module.

In a possible design, the first switching condition includes: the data obtained by the first detection module is invalid.

In a possible design, that the data obtained by the first detection module is invalid includes: the processing module determines that a value by which an altitude value of the electronic device increases within first preset duration is greater than a preset first height threshold.

In a possible design, the processing module is further configured to: determine whether a second switching condition is met; and if it is determined that the second switching condition is met, determine that the display module is to display the altitude obtained by the first detection module.

In a possible design, the second switching condition includes: the data obtained by the first detection module becomes valid again.

In a possible design, that the data obtained by the first detection module becomes valid again includes: the processing module determines that an absolute value of a difference between the altitude obtained by the first detection module and the altitude obtained by the second detection module is less than a preset threshold.

In a possible design, that the data obtained by the first detection module becomes valid again includes: the processing module determines that a value by which the altitude value of the electronic device decreases within second preset duration is greater than a preset second height threshold.

In a possible design, the second switching condition includes: the processing module determines that an operation of disabling the second detection module by a user is detected.

In a possible design, the first detection module is a barometric pressure sensor, and the second detection module is a GNSS module.

In a possible design, the processing module is further configured to determine to enable a GNSS function of the GNSS module.

In a possible design, the processing module is further configured to determine that the GNSS module is to periodically enable the GNSS function based on a preset first time interval.

According to a third aspect, an embodiment of this application provides a computer storage medium. The computer storage medium includes computer instructions, and when the computer instructions run on an electronic device, the electronic device performs the method for measuring a height on a plane according to the first aspect and the possible design manners of the first aspect.

According to a fourth aspect, an embodiment of this application provides a computer program product. When the computer program product runs on a computer, the computer performs the method for measuring a height on a plane according to the first aspect and the possible design manners of the first aspect.

The electronic device in the second aspect, the computer storage medium in the third aspect, and the computer program product in the fourth aspect are all configured to perform the corresponding method provided above. Therefore, for beneficial effects that can be achieved by the electronic device, the computer storage medium, and the computer program product, refer to beneficial effects of a corresponding solution in the corresponding method provided above. Details are not described herein again.

DESCRIPTION OF EMBODIMENTS

The method for measuring a height on a plane provided in the embodiments of this application may be applied to an electronic device with an "altimeter" function. The electronic device may be a wearable device (for example, a smart watch, a smart band, smart glasses, or a smart helmet), a portable computer (for example, a mobile phone), a notebook computer, a tablet computer, an augmented reality (augmented reality, AR)/a virtual reality (virtual reality, VR) device, or the like. A specific form of the electronic device is not specially limited in the embodiments of this application.

Figure 2A:
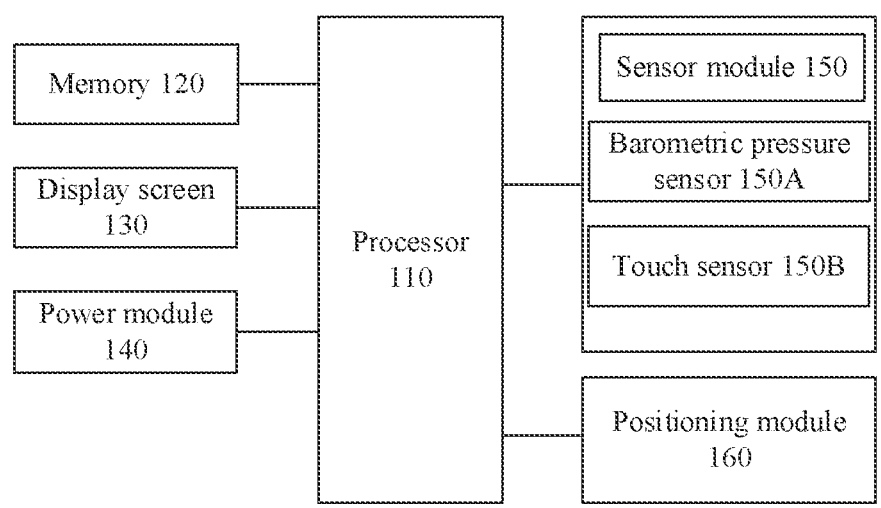
FIG. 2A is a schematic composition diagram 1 of a structure of an electronic device according to an embodiment of this application.

FIG. 2A is a schematic diagram of a structure of an electronic device 100 according to an embodiment of this application. The electronic device 100 may include a processor 110, a memory 120, a display 130, a power module 140, a sensor module 150, a positioning module 160, and the like. The sensor module 150 may include a barometric pressure sensor 150A, a touch sensor 150B, and the like.

It may be understood that the structure shown in this embodiment of the present invention does not constitute a specific limitation on the electronic device 100. In other embodiments of this application, the electronic device 100 may include more or fewer components than those shown in the figure, combine some components, split some components, or have different component arrangements. The components shown in the figure may be implemented by hardware, software, or a combination of software and hardware.

The processor 110 may include one or more processors. For example, the processor 110 may include an application processor, a controller, a digital signal processor (digital signal processor, DSP), or the like. Different processors may be independent components, or may be integrated into one or more processors.

The controller may be a nerve center and a command center of the electronic device 100. The controller may generate an operation control signal based on an instruction operation code and a time sequence signal, to complete control of instruction fetching and instruction execution.

An operating system of the electronic device 100 may be installed on the application processor, to manage hardware and software resources of the electronic device 100, for example, manage and configure memory, prioritize supply and demand of system resources, control input and output devices, operate a network, manage a file system, and manage a driver. The operating system may also be configured to provide an operating interface for a user to interact with the system. Various types of software, such as a driver and an application (application, App), may be installed in the operating system.

The memory 120 is configured to store instructions and data. In some embodiments, the memory 120 is a cache memory. The memory may store instructions or data used or cyclically used by the processor 110. If the processor 110 needs to use the instructions or the data again, the processor 110 may directly invoke the instructions or the data from the memory 120. This avoids repeated access, reduces a waiting time of the processor 110, and improves system efficiency.

In some embodiments, the memory 120 may alternatively be disposed in the processor 110. In other words, the processor 110 includes the memory 120. This is not limited in this embodiment of this application.

The display 130 is configured to display an image, a video, and the like. The display 130 includes a display panel. The display panel may be a liquid crystal display (liquid crystal display, LCD), an organic light-emitting diode (organic light-emitting diode, OLED), an active-matrix organic light-emitting diode (active-matrix organic light emitting diode, AMOLED), a flexible light-emitting diode (flex light-emitting diode, FLED), a mini-LED, a micro-LED, a micro-OLED, quantum dot light emitting diodes (quantum dot light emitting diodes, QLED), or the like. In some embodiments, the electronic device 100 may include one or N displays 130, where N is a positive integer greater than 1.

The power module 140 may be configured to supply power to each component included in the electronic device 100. In some embodiments, the power module 140 may be a battery, for example, a rechargeable battery.

The barometric pressure sensor 150A is configured to measure barometric pressure. In this embodiment of this application, the electronic device 100 calculates an altitude by using the barometric pressure value measured by the barometric pressure sensor 150A. In an example, the electronic device 100 calculates the altitude based on the barometric pressure value measured by the barometric pressure sensor 150A and a barometric formula. The barometric formula is a formula that describes how barometric pressure changes with a height. For a specific method for calculating the height based on the barometric pressure value and the barometric formula, refer to descriptions in the conventional technology. Details are not described in this embodiment of this application.

The touch sensor 150B is also referred to as a "touch panel". The touch sensor 150B may be disposed in the display 130. The touch sensor 150B and the display 130 constitute a touchscreen. The touch sensor 150B is configured to detect a touch operation performed on or near the touch sensor 150B. The touch sensor may transfer the detected touch operation to the application processor, to determine a type of a touch event. The display 130 may provide a visual output related to the touch operation. In some other embodiments, the touch sensor 150B may alternatively be disposed on a surface of the electronic device 100 at a location different from that of the display 130.

The positioning module 160 is configured to position the electronic device 100. In this embodiment of this application, the positioning module 160 may receive data of a global navigation satellite system (global navigation satellite system, GNSS). The data of the GNSS includes a longitude, a latitude, an altitude, and the like. The electronic device 100 may obtain the altitude of the electronic device 100 by using altitude data of the GNSS. The GNSS may include a global positioning system (global positioning system, GPS), a global navigation satellite system (global navigation satellite system, GLONASS), a BeiDou navigation satellite system (beidou navigation satellite system, BDS), a quasi-zenith satellite system (quasi-zenith satellite system, QZSS), a Galileo satellite navigation system (galileo satellite navigation system, GSNS), and/or a satellite based augmentation system (satellite based augmentation systems, SBAS).

The method for measuring a height on a plane provided in the embodiments of this application may be applied to the electronic device 100. The electronic device 100 has an "altimeter" function, and can display a current altitude of the electronic device 100 on the display 130. The electronic device 100 may obtain the altitude of the electronic device 100 by using the barometric pressure value measured by the barometric pressure sensor 150A; or the electronic device 100 may obtain the altitude of the electronic device 100 by using the altitude data received by the positioning module 160. Generally, because the altitude obtained by using the barometric pressure value measured by the barometric pressure sensor is more accurate than the altitude obtained by receiving the data of the GNSS by the electronic device, a height value displayed on the display 130 is the altitude obtained by using the barometric pressure sensor 150A. When the electronic device 100 determines that the altitude data obtained by using the barometric pressure sensor 150A is untrustworthy, the display 130 displays the altitude received by the positioning module 160. In this way, the electronic device 100 can also display an accurate altitude when the data of the barometric pressure sensor is untrustworthy in a case in which a user takes a plane or in another case. Certainly, a function of displaying the current altitude on the display 130 by the electronic device 100 may be another name, and the electronic device 100 does not display a word "Altimeter" on the display 130. For example, "Altitude: XX meters" is displayed on the display 130 of the electronic device 100.

In some embodiments, the barometric pressure sensor and/or the positioning module of the electronic device 100 may not be disposed on the electronic device 100, in other words, the electronic device 100 may obtain the current altitude by using a barometric pressure sensor and/or a positioning module of another device (an electronic device 200) connected to the electronic device 100, and display the current altitude on the electronic device 100.

Figure 2B:
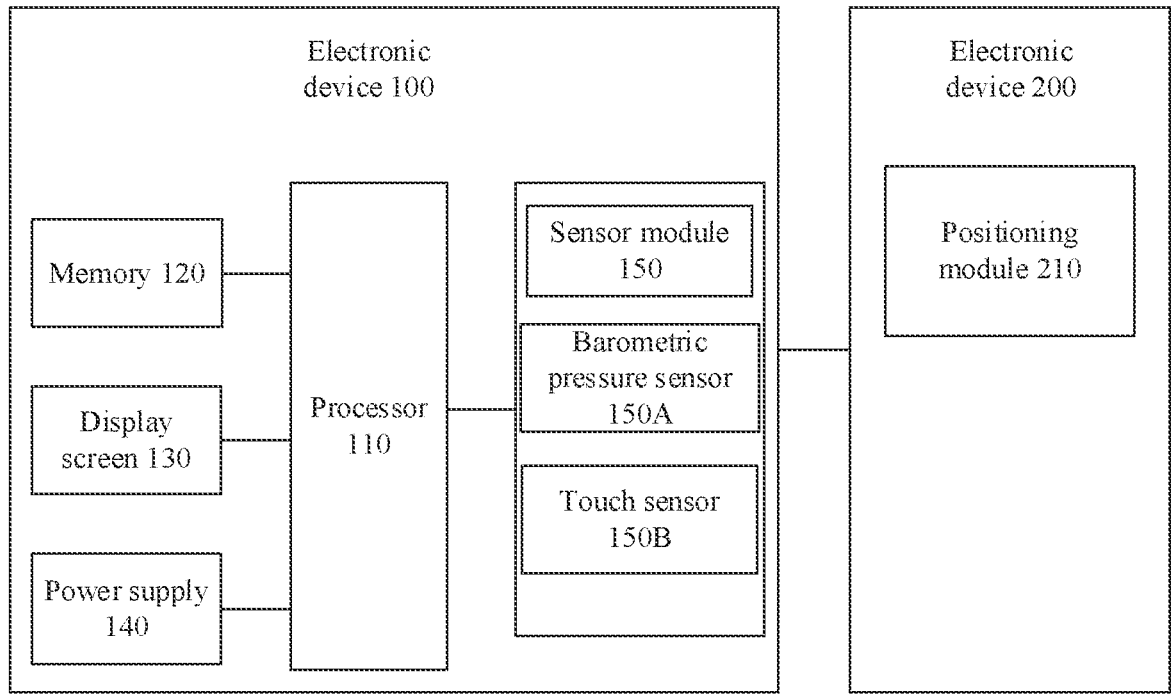
FIG. 2B is a schematic composition diagram 2 of a structure of an electronic device according to an embodiment of this application.

In an example, as shown in FIG. 2B, an electronic device 100 and an electronic device 200 are wirelessly connected. The electronic device 100 includes a processor 110, a memory 120, a display 130, a power module 140, a sensor module 150, and the like. The electronic device 200 includes a positioning module 210, and the positioning module 210 may receive data of a GNSS, The electronic device 100 may obtain an altitude of the electronic device 100 by using a barometric pressure value measured by a barometric pressure sensor 150A of the sensor module 150; or may receive altitude data of the positioning module 210 of the electronic device 200, and obtain an altitude of the electronic device 200, in other words, obtain an altitude of the electronic device 100.

Figure 2C:
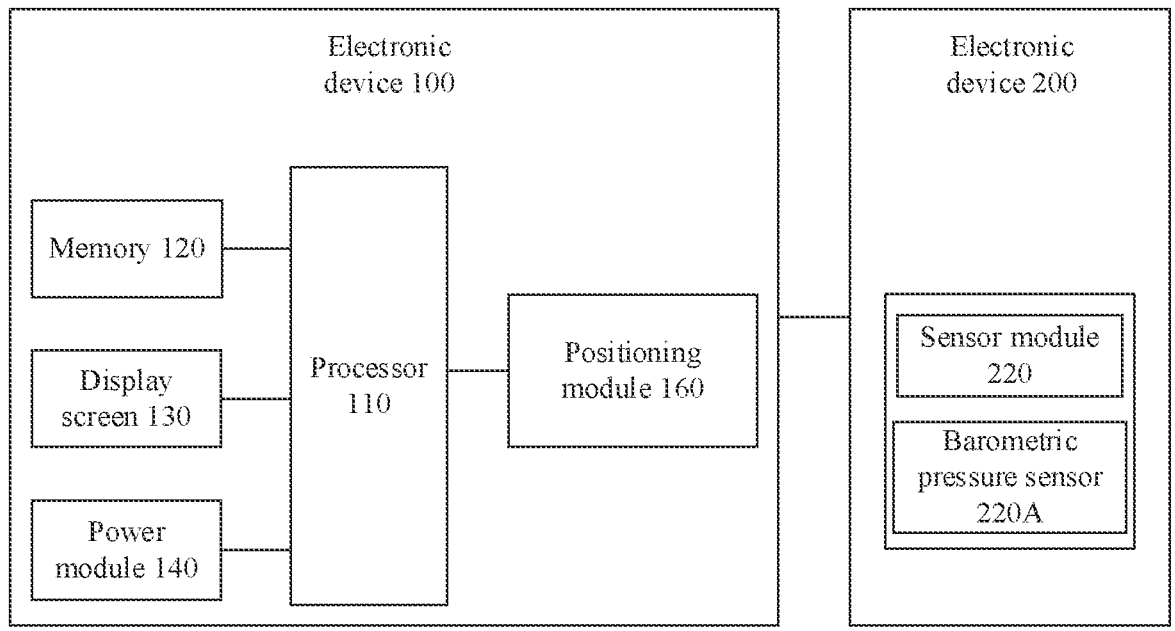
FIG. 2C is a schematic composition diagram 3 of a structure of an electronic device according to an embodiment of this application.

In another example, as shown in FIG. 2C, an electronic device 100 and an electronic device 200 are wirelessly connected. The electronic device 100 includes a processor 110, a memory 120, a display 130, a power module 140, a positioning module 160, and the like. The electronic device 200 includes a sensor module 220, and the sensor module 220 includes a barometric pressure sensor 220A, configured to measure barometric pressure. The electronic device 100 may obtain an altitude of the electronic device 100 by using altitude data received by the positioning module 160; or may receive barometric pressure value data of the barometric pressure sensor 220A of the sensor module 220 of the electronic device 200, and obtain an altitude of the electronic device 200 based on the received barometric pressure value data, in other words, obtain an altitude of the electronic device 100.

Figure 2D:
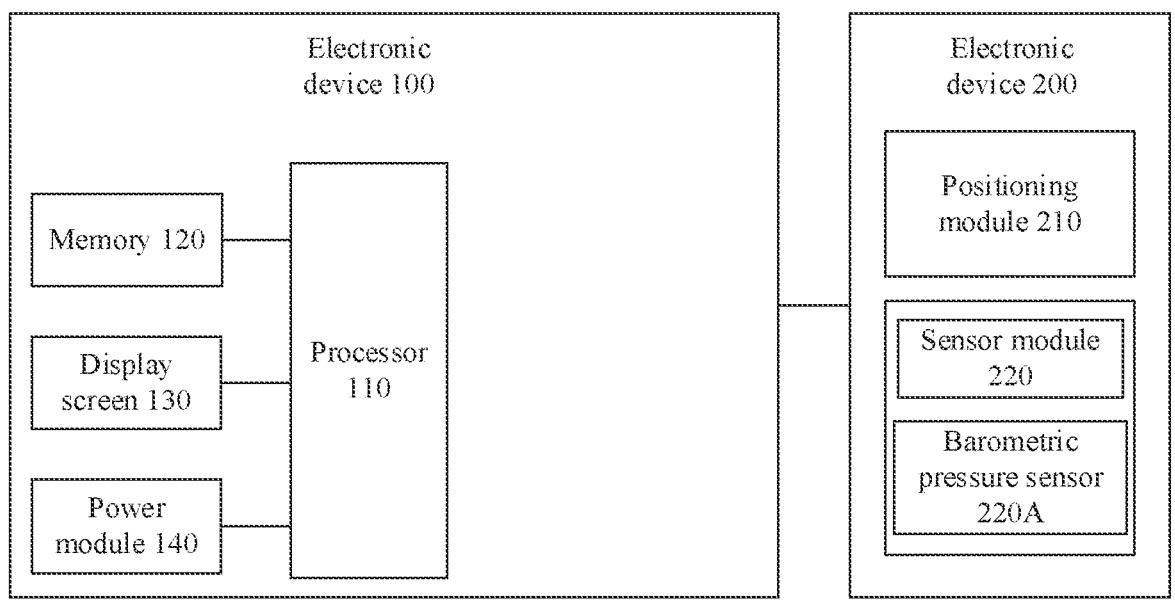
FIG. 2D is a schematic composition diagram 4 of a structure of an electronic device according to an embodiment of this application.

In still another example, as shown in FIG. 2D, an electronic device 100 and an electronic device 200 are wirelessly connected. The electronic device 100 includes a processor 110, a memory 120, a display 130, a power module 140, and the like. The electronic device 200 includes a positioning module 210, a sensor module 220, and the like, and the sensor module 220 includes a barometric pressure sensor 220A. The positioning module 210 may receive data of a GNSS. The barometric pressure sensor 220A is configured to measure barometric pressure. The electronic device 100 may receive barometric pressure value data of the barometric pressure sensor 220A of the sensor module 220 of the electronic device 200, and obtain an altitude of the electronic device 200 based on the received barometric pressure value data, in other words, obtain an altitude of the electronic device 100; or may receive altitude data of the positioning module 210 of the electronic device 200, and obtain an altitude of the electronic device 200, in other words, obtain an altitude of the electronic device 100.

For example, the electronic device 100 is a smart watch, and the electronic device 200 is a mobile phone; or the electronic device 100 is a mobile phone, and the electronic device 200 is a smart watch.

With reference to the accompanying drawings, the following describes in detail the method for measuring a height on a plane provided in the embodiments of this application.

The embodiments of this application are descried by using an example in which the electronic device 100 is a smart watch and the smart watch includes a structure shown in FIG. 2A, it may be understood that the method for measuring a height on a plane provided in the embodiments of this application is also applicable to the electronic device 100 in FIG. 2B, FIG. 2C, or FIG. 2D.

Figure 3:
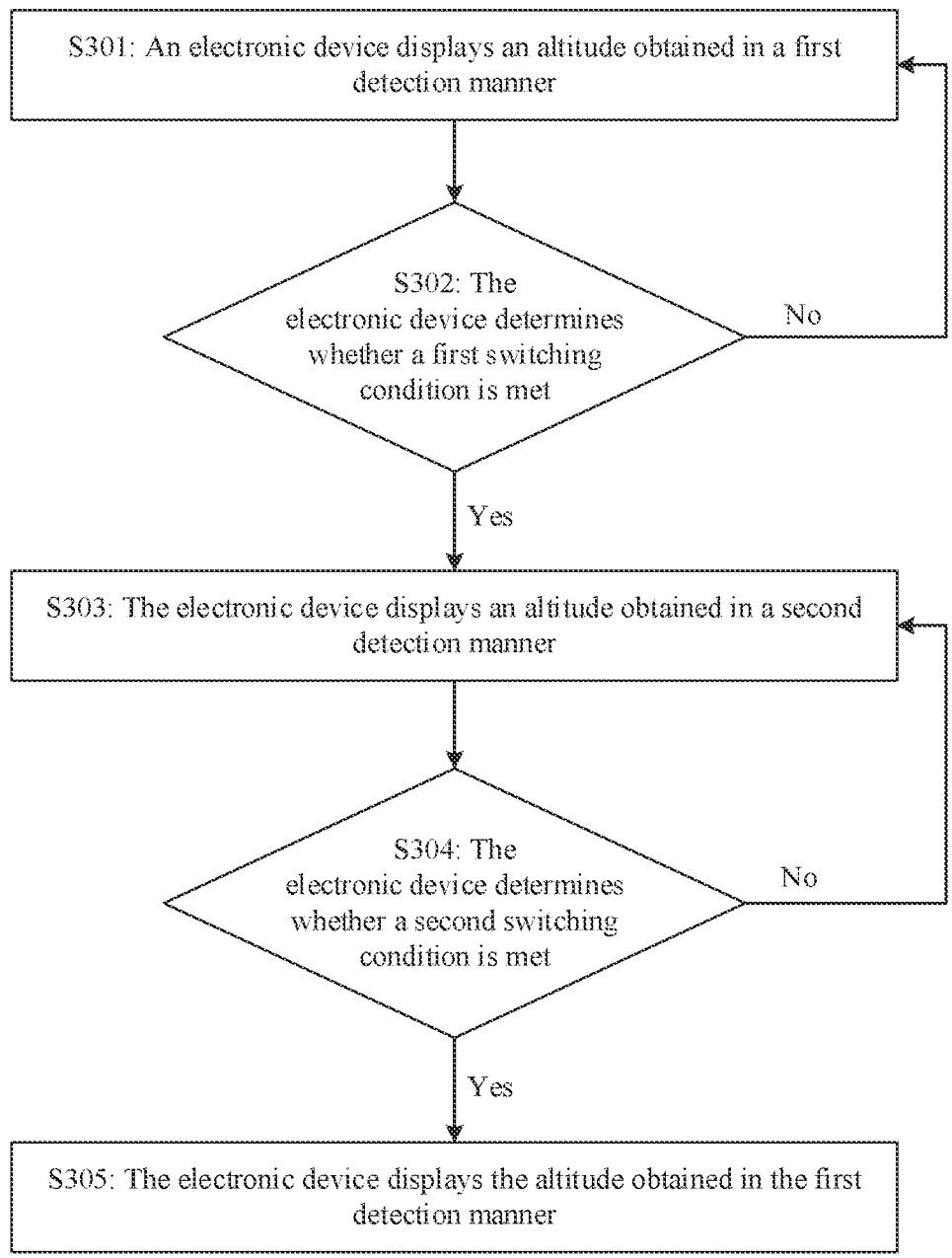
FIG. 3 is a flowchart 1 of a method for measuring a height on a plane according to an embodiment of this application.

As shown in FIG. 3, a method for measuring a height on a plane provided in an embodiment of this application may include the following steps.

S301: An electronic device displays an altitude obtained in a first detection manner.

The first detection manner may be a default altitude detection manner of the electronic device. For example, the first detection manner is a manner of detecting an altitude by using a barometric pressure sensor. The electronic device obtains a current altitude based on a barometric pressure value measured by the barometric pressure sensor.

Figure 1:
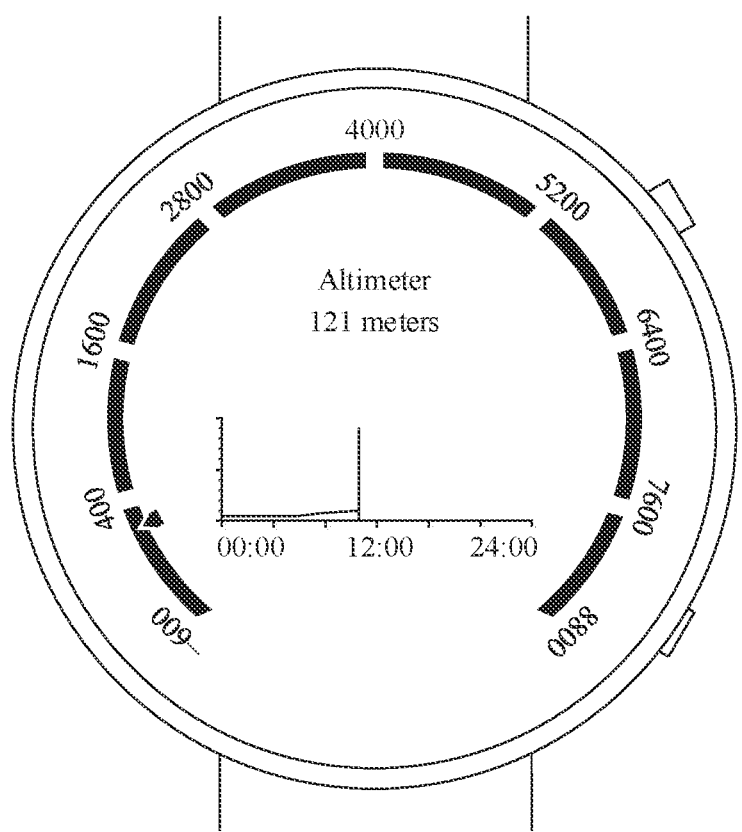
FIG. 1 is a schematic diagram 1 of an example of a display interface of an electronic device according to an embodiment of this application.

For example, when a user does not take a plane, the electronic device displays the current altitude obtained based on the barometric pressure value measured by the barometric pressure sensor. For example, the electronic device displays an interface shown in FIG. 1, and a value of the current altitude is 121 meters.

S302: The electronic device determines whether a first switching condition is met; and if the electronic device determines that the first switching condition is met, the electronic device performs S303 that the electronic device displays an altitude obtained in a second detection manner; or if the electronic device determines that the first switching condition is not met, the electronic device performs S301 that the electronic device displays the altitude obtained in the first detection manner.

The first switching condition is that the data of the barometric pressure sensor is invalid.

For example, the user takes a plane with the electronic device, and the plane takes off. After the plane takes off, pressure is boosted in a cabin of the plane, and the barometric pressure value detected by the barometric pressure sensor of the electronic device is inconsistent with an atmospheric pressure value corresponding to the altitude of the electronic device, in other words, the data of the barometric pressure sensor is invalid.

If the electronic device detects that a first preset condition is met, the electronic device determines that the data of the barometric pressure sensor is invalid.

In an implementation, the first preset condition is that a value by which the altitude value of the electronic device increases within first preset duration is greater than a preset first height threshold. For example, the first preset duration is 30 seconds, and the first height threshold is 100 meters. The altitude of the electronic device is obtained in the first detection manner.

If the electronic device detects that the value by which the altitude value of the electronic device increases within the first preset duration is greater than the preset first height threshold, the electronic device determines that the plane takes off, because after the plane takes off, pressure is boosted in the cabin of the plane, and the barometric pressure value detected by the barometric pressure sensor of the electronic device is inconsistent with the atmospheric pressure value corresponding to the altitude of the electronic device, in other words, the data of the barometric pressure sensor of the electronic device is invalid.

S303: The electronic device displays the altitude obtained in the second detection manner.

The second detection manner is a detection manner different from the first detection manner. For example, the second detection manner is a manner of detecting an altitude by using a GNSS, The electronic device receives altitude data in data of the GNSS, to obtain the current altitude.

Figure 4:
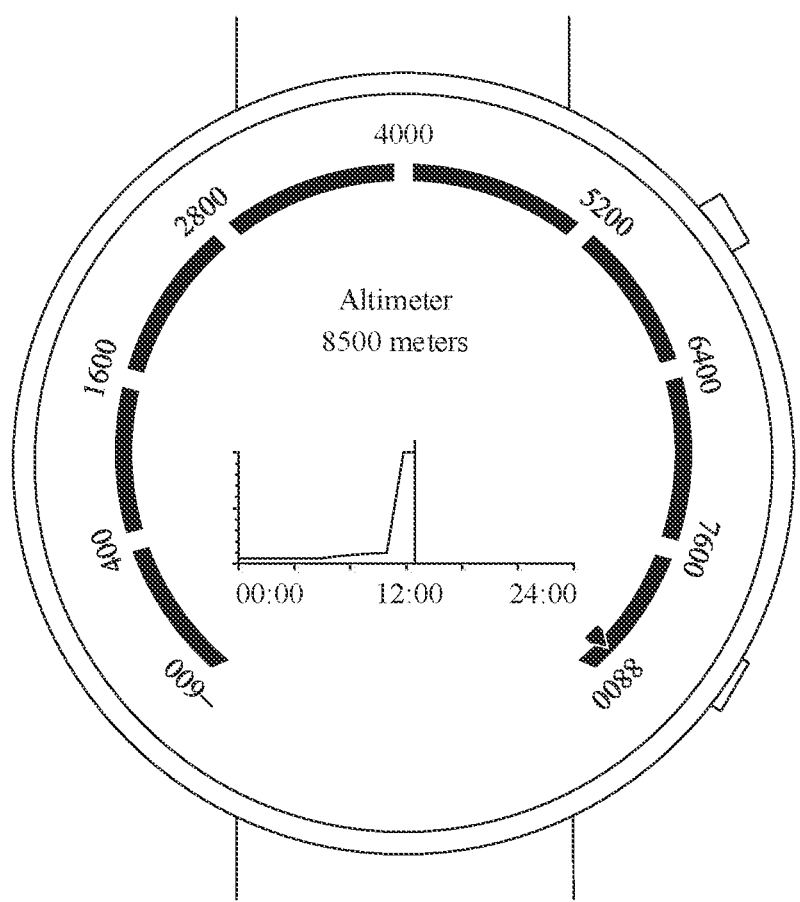
FIG. 4 is a schematic diagram 2 of an example of a display interface of an electronic device according to an embodiment of this application.

For example, after the plane takes off, a smart watch displays the altitude data in the received data of the GNSS. As shown in FIG. 4, the smart watch displays a current altitude 8500 meters.

A GNSS function of the electronic device has an enabled state and a disabled state. In the enabled state, the electronic device may receive the data of the GNSS, and in the disabled state, the electronic device does not receive the data of the GNSS.

In some embodiments, if the electronic device determines, after determining that the data of the barometric pressure sensor is invalid, that the GNSS function of the electronic device is in the enabled state, the electronic device may directly display the altitude in the received data of the GNSS.

Before the plane takes off, the user may enable the GNSS function in some scenarios. For example, the GNSS is a GPS. If the electronic device determines, after determining that the data of the barometric pressure sensor is invalid, that a GPS function of the electronic device is in the enabled state, the electronic device may directly display height data in received data of the GPS.

In an implementation, the electronic device may enable the GPS function by enabling some modes such as a sports mode. For example, if the electronic device determines that the user has enabled an outdoor sports mode, the electronic device enables the GPS function. The user may enable the outdoor sports mode by enabling a sports mode of the electronic device. The sports mode of the electronic device may include walking, outdoor running, indoor running, riding, indoor cycling, mountain climbing, and the like. In an implementation, the outdoor sports mode includes walking, outdoor running, riding, and mountain climbing in the sports mode. It should be noted that the sports mode of the electronic device may have another name. For example, in some electronic devices, enabling the sports mode is referred to as enabling one "single motion". This is not limited in this embodiment of this application.

If the electronic device determines that the electronic device receives an operation of enabling the sports mode such as walking, outdoor running, riding, or mountain climbing by the user, in other words, the user has enabled the outdoor sports mode, the electronic device enables the GPS function.

In an example, the user may enable the sports mode on the smart watch. In another example, the user may enable the sports mode on a mobile phone on which a smart watch management APP is installed.

Figure 5A:
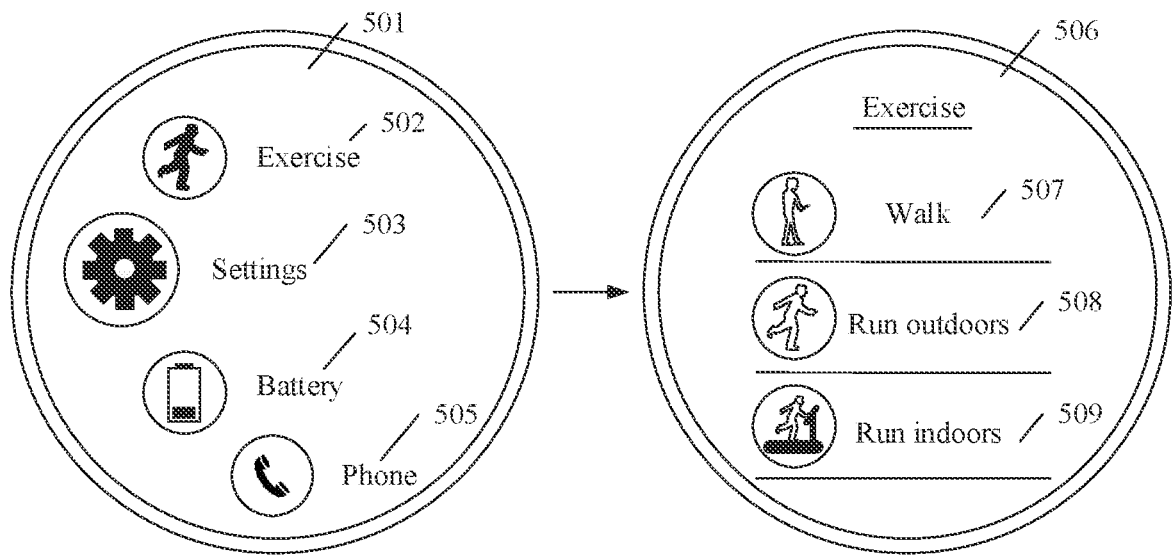
FIG. 5A is a schematic diagram 3 of an example of a display interface of an electronic device according to an embodiment of this application.

For example, as shown in FIG. 5A, the user may set each setting item of the smart watch in an interface 501 of the smart watch. The interface 501 includes an "Exercise" option 502, a "Settings" option 503, a "Battery" option 504, and a "Phone" option 505. The "Exercise" option 502 is used to set a sports mode, and different sports modes may be used to detect different sports types. The "Settings" option 503 is used to set various common options and applications of the smart watch, for example, may include setting a watch face style, a font size, and a volume. The "Battery" option 504 is used to set and view a battery, for example, set the battery to a power saving mode and view remaining battery power. The "Phone" option 505 is used to set a phone application, for example, set a call volume. The smart watch may receive a tap operation performed by the user on the "Exercise" option 502, and the smart watch displays an exercise interface 506 in response to the tap operation performed by the user on the "Exercise" option 502. The exercise interface 506 includes a "Walk" option 507, a "Run outdoors" option 508, and a "Run indoors" option 509, The user may enable a walking mode by tapping the "Walk" option 507, enable an outdoor running mode by tapping the "Run outdoors" option 508, and enable an indoor running mode by tapping the "Run indoors" option 509. For example, the smart watch may receive a tap operation performed by the user on the "Run outdoors" option 508, and the smart watch enables the outdoor running mode in response to the tap operation performed by the user on the "Run outdoors" option 508.

It may be understood that options included in the foregoing interfaces are described merely as examples. For example, the interface 501 may further include a "Timer" option and a "Music" option, and the exercise interface 506 may further include a "Ride" option, a "Cycle indoors" option, and a "Climb a mountain" option. Details are not described in this embodiment of this application. The user may trigger the smart watch to display another option in the interface by using a preset gesture. For example, the preset gesture may be that a finger slides up or a finger slides down.

In another implementation, the sports mode may further include taking a plane, if the electronic device determines that the user has enabled "Take a plane" in the sports mode, in other words, determines that the electronic device receives an operation of enabling "Take a plane" in the sports mode, the electronic device enables the GPS function.

Figure 5B:
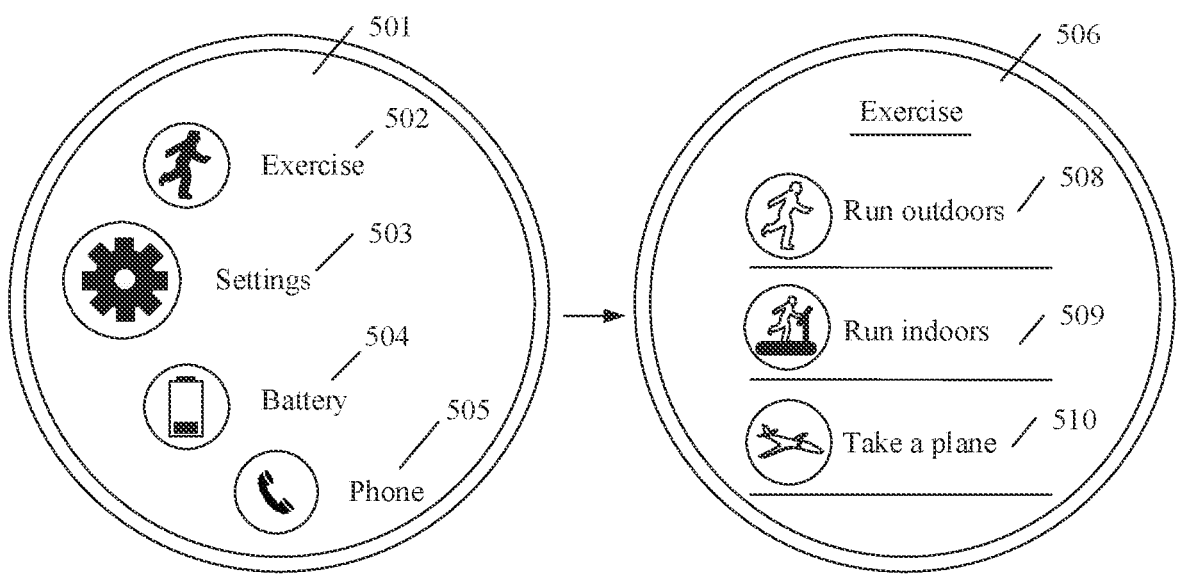
FIG. 5B is a schematic diagram 4 of an example of a display interface of an electronic device according to an embodiment of this application.

For example, as shown in FIG. 5B, the smart watch receives, in an interface 501, a tap operation performed by the user on an "Exercise" option 502, and the smart watch displays an exercise interface 506 in response to the tap operation performed by the user on the "Exercise" option 502. The exercise interface 506 includes a "Take a plane" option 510, and the user may enable a "Take a plane" mode by tapping the "Take a plane" option 510. The smart watch may receive a tap operation performed by the user on the "Take a plane" option 510, and the smart watch enables the "Take a plane" mode in response to the tap operation performed by the user on the "Take a plane" option 510.

In another example, the user may set an option of the GNSS function of the smart watch or the mobile phone, to enable or disable the GNSS function. Taking the mobile phone as an example, the user may set an option of a positioning function on the mobile phone, to enable or disable the positioning function (that is, enable or disable the GPS).

Figure 5C:
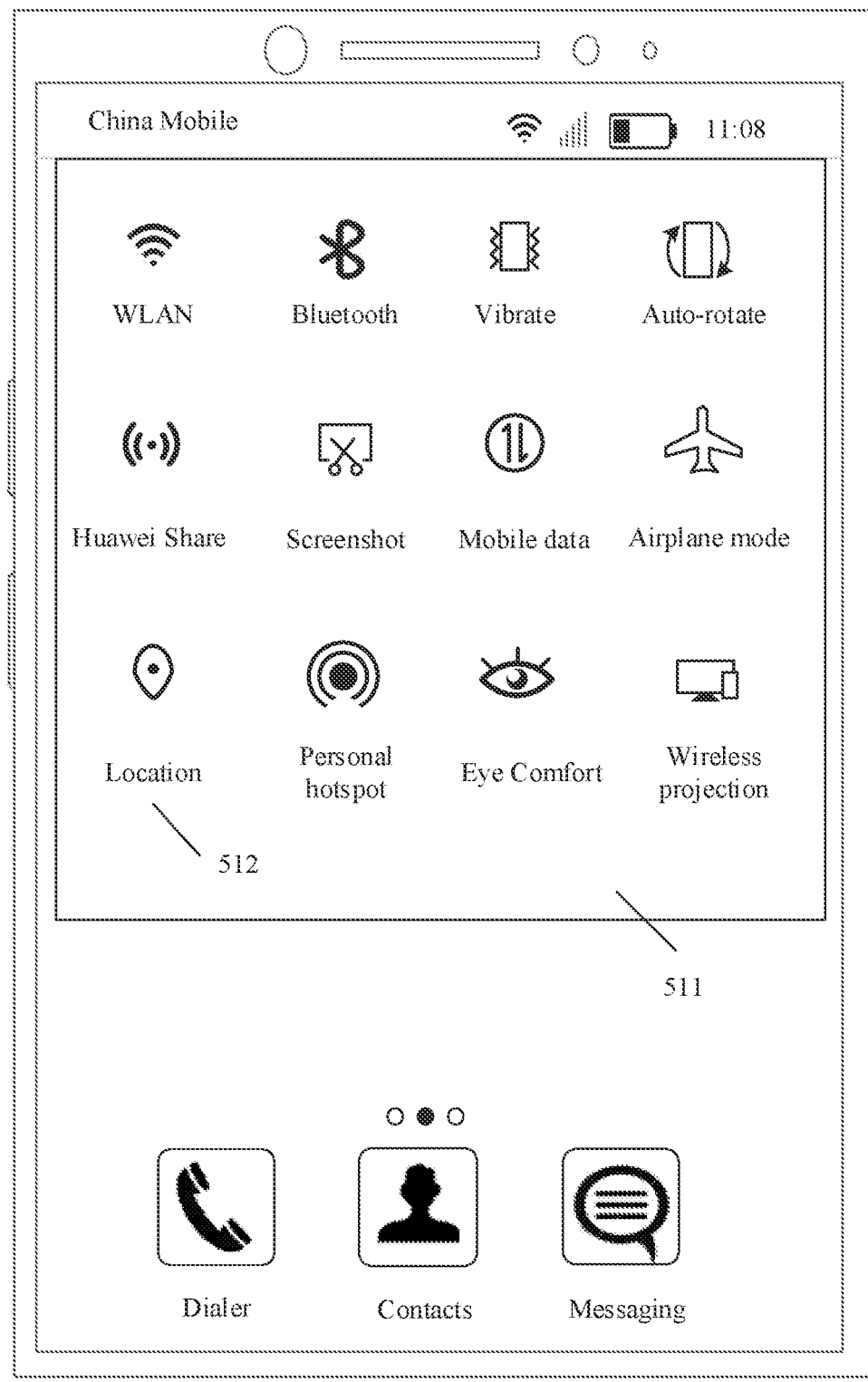
FIG. 5C is a schematic diagram 5 of an example of a display interface of an electronic device according to an embodiment of this application.

For example, as shown in FIG. 5C, the mobile phone may receive a first gesture of the user on a desktop, and display a pull-down menu 511. For example, the first gesture may be that a single finger slides down from the top of a screen. The pull-down menu 511 includes options such as a WLAN option, a Bluetooth option, a vibrate option, a location option 512, and a wireless projection option. The user may enable or disable a corresponding function by tapping an option. The location option 512 is used to control a positioning function of the mobile phone to be enabled or disabled. For example, when the positioning function of the mobile phone is disabled, if the mobile phone receives a tap operation performed by the user on the location option 512, the mobile phone enables the positioning function; or when the positioning function of the mobile phone is enabled, if the mobile phone receives a tap operation performed by the user on the location option 512, the mobile phone disables the positioning function. For a function of another option in the pull-down menu 511, refer to function descriptions in the conventional technology. This is not limited in this embodiment of this application, and details are not described herein.

In some embodiments, if the electronic device determines, after determining that the data of the barometric pressure sensor is invalid, that the GNSS function of the electronic device is in the disabled state, the electronic device enables the GNSS function of the electronic device, and displays the altitude in the received data of the GNSS.

In an implementation, the electronic device periodically enables the GNSS function based on a preset first time interval. In each period, the GNSS function is disabled after the enabled state of the GNSS function lasts for preset duration. For example, the preset first time interval may be 10 minutes, and the preset duration is 30 seconds. For example, the GNSS is a GPS. The electronic device enables a GPS function every 10 minutes to receive an altitude in data of the GPS. The electronic device disables the GPS function after the GPS function has been enabled for 30 seconds. Within the first time interval before the GPS function is enabled next time, the electronic device displays an altitude in data of the GPS that is received this time. Compared with a case in which the GNSS function is always in the enabled state, intermittently enabling and disabling the GNSS function can reduce power consumption of the electronic device.

S304: The electronic device determines whether a second switching condition is met; and if the electronic device determines that the second switching condition is met, the electronic device performs S305 that the electronic device displays the altitude obtained in the first detection manner, or if the electronic device determines that the second switching condition is not met, the electronic device performs S303 that the electronic device displays the altitude obtained in the second detection manner.

In a scenario, when the plane that the user takes lands, pressure is no longer boosted in the cabin of the plane, and the electronic device detects that the data of the barometric pressure sensor becomes valid again, and in this case, the electronic device may stop displaying the altitude in the received data of the GNSS, and display the altitude obtained based on the barometric pressure value measured by the barometric pressure sensor. The second switching condition is that the electronic device determines that the data of the barometric pressure sensor is valid.

The electronic device may stop receiving the data of the GNSS. For example, the electronic device stops periodically enabling the GNSS function based on the preset first time interval.

After the plane lands, the barometric pressure value detected by the barometric pressure sensor of the electronic device is inconsistent with the atmospheric pressure value corresponding to the altitude of the electronic device, in other words, the data of the barometric pressure sensor is valid.

In an implementation, if the electronic device detects that a second preset condition is met, the electronic device determines that the data of the barometric pressure sensor is valid.

In a possible design, the second preset condition is that an absolute value of a difference between the altitude obtained by the electronic device based on the barometric pressure value measured by the barometric pressure sensor and the altitude in the received data of the GNSS is less than a preset threshold. For example, the preset threshold may be 100 meters.

For example, the electronic device periodically compares, based on a preset second time interval, the altitude obtained based on the barometric pressure value measured by the barometric pressure sensor and the altitude in the received data of the GNSS. If the electronic device determines, M (M>1) consecutive times, that the absolute value of the difference between the altitude obtained based on the barometric pressure value measured by the barometric pressure sensor and the altitude in the received data of the GNSS is less than the preset threshold, the electronic device determines that the data of the barometric pressure sensor is valid.

In an example, the electronic device periodically enables the GNSS function based on the preset first time interval. Each time the electronic device enables the GNSS function and receives the data of the GNSS, the electronic device obtains the altitude based on the barometric pressure value measured by the barometric pressure sensor, and compares the altitude obtained based on the barometric pressure value measured by the barometric pressure sensor and the altitude in the received data of the GNSS. In this example, the second time interval is the same as the first time interval.

For example, the smart watch enables the GPS function for the first time, receives data of the GPS, determines that an altitude is 500 meters, obtains an altitude 560 meters based on a barometric pressure value measured by the barometric pressure sensor, and determines that a difference between the two altitudes is less than 100 meters. After 10 minutes, the smart watch enables the GPS function for the second time, receives data of the GPS, determines that an altitude is 180 meters, obtains an altitude 210 meters based on a barometric pressure value measured by the barometric pressure sensor, and determines that a difference between the two altitudes is less than 100 meters. After 10 minutes, the smart watch enables the GPS function for the third time, receives data of the GPS, determines that an altitude is 270 meters, obtains an altitude 210 meters based on a barometric pressure value measured by the barometric pressure sensor, and determines that a difference between the two altitudes is less than 100 meters. The smart watch determines, three consecutive times (M=3), that an absolute value of the difference between the altitude obtained based on the barometric pressure value measured by the barometric pressure sensor and the altitude in the received data of the GPS is less than the preset threshold (100 meters), and in this case, determines that the data of the barometric pressure sensor is valid.

In another example, the GNSS function of the smart watch remains in the enabled state. For example, the user enables the "Take a plane" mode. The electronic device periodically compares, based on a preset second time interval, the altitude obtained based on the barometric pressure value measured by the barometric pressure sensor and the altitude in the received data of the GNSS. The second time interval may be the same as or different from the first time interval.

For example, the GPS function of the smart watch is in the enabled state, and the smart watch receives data of the GPS every 2 seconds. For the first time, the smart watch determines, based on received data of the GPS, that an altitude is 500 meters, obtains an altitude 560 meters based on a barometric pressure value measured by the barometric pressure sensor, and determines that a difference between the two altitudes is less than 100 meters. After 2 seconds, the smart watch determines, based on received data of the GPS, that an altitude is 480 meters, obtains an altitude 550 meters based on a barometric pressure value measured by the barometric pressure sensor, and determines that a difference between the two altitudes is less than 100 meters. After 2 seconds, the smart watch determines, based on received data of the GPS, that an altitude is 470 meters, obtains an altitude 500 meters based on a barometric pressure value measured by the barometric pressure sensor, and determines that a difference between the two altitudes is less than 100 meters. The smart watch determines, three consecutive times (M=3), that an absolute value of the difference between the altitude obtained based on the barometric pressure value measured by the barometric pressure sensor and the altitude in the received data of the GPS is less than the preset threshold (100 meters), and in this case, determines that the data of the barometric pressure sensor is valid.

In another implementation, if the electronic device detects that a third preset condition is met, the electronic device determines that the data of the barometric pressure sensor is valid.

In a possible design, the third preset condition is that a value by which the altitude value of the electronic device decreases within second preset duration is greater than a preset second height threshold. For example, the second preset duration is 30 seconds, and the second height threshold is 200 meters. The altitude of the electronic device is obtained in the second detection manner. If the electronic device detects that the value by which the altitude value of the electronic device decreases within the second preset duration is greater than the preset second height threshold, the electronic device determines that the plane that the user takes lands, and in this case, the data of the barometric pressure sensor becomes valid again.

For example, the GNSS function of a smart watch remains in the enabled state, and the electronic device receives the altitude data in the data of the GNSS, to obtain the current altitude. If the electronic device determines that the value by which the altitude value of the electronic device decreases within the second preset duration is greater than the preset second height threshold, the electronic device determines that the data of the barometric pressure sensor is valid.

In a scenario, the user may disable the GNSS function in a flight process of the plane, and the electronic device stops receiving the data of the GNSS, stops displaying the altitude in the received data of the GNSS, and displays the altitude obtained based on the barometric pressure value measured by the barometric pressure sensor. The second switching condition is that the electronic device determines that the user has disabled the GNSS function.

For example, if the user disables the outdoor sports mode such as walking, outdoor running, riding, or mountain climbing on the smart watch in the flight process of the plane, the smart watch may disable the GNSS function. This scenario is particularly applicable to a case in which the user enables the GNSS function by enabling the outdoor sports mode.

For example, if the user disables the "Take a plane" mode on the smart watch in the flight process of the plane, the smart watch may also disable the GNSS function.

For example, if the user disables the positioning function of the mobile phone in the flight process of the plane, the GNSS function is disabled.

In a scenario, the user may disable the GNSS function in the flight process of the plane. If the electronic device determines that the data of the barometric pressure sensor is invalid in this case, the electronic device enables the GNSS function of the electronic device. For example, the electronic device periodically enables the GNSS function based on the preset first time interval. In this way, the electronic device can display the altitude in the received data of the GNSS.

Subsequently, when the plane that the user takes lands, pressure is no longer boosted in the cabin of the plane, and the electronic device detects that the data of the barometric pressure sensor becomes valid again, and in this case, the electronic device may stop displaying the altitude in the received data of the GNSS, and display the altitude obtained based on the barometric pressure value measured by the barometric pressure sensor. In addition, the electronic device stops receiving the data of the GNSS. For example, the electronic device stops periodically enabling the GNSS function based on the preset first time interval.

In this scenario, the second switching condition is that the electronic device determines that the data of the barometric pressure sensor is valid.

In an implementation, after determining, in S302, that the data of the barometric pressure sensor is invalid, the electronic device may record that the barometric pressure sensor is in an invalid state. Subsequently, if the electronic device detects that the data of the barometric pressure sensor becomes valid again, the electronic device records that the barometric pressure sensor is in a valid state. For example, the electronic device may record and update a state identifier of the barometric pressure sensor. The state identifier of the barometric pressure sensor is used to indicate a status of the barometric pressure sensor. If the state identifier of the barometric pressure sensor is 0, it indicates that the data of the barometric pressure sensor is valid. If the state identifier of the barometric pressure sensor is 1, it indicates that the data of the barometric pressure sensor is invalid.

In an example, the data of the barometric pressure sensor of the smart watch is valid, the smart watch displays the altitude obtained based on the barometric pressure value measured by the barometric pressure sensor, and the state identifier of the barometric pressure sensor is 0. If the user enables the "Take a plane" mode on the smart watch, the GPS function is enabled. Subsequently, the user takes a plane with the smart watch, and the plane takes off. After the plane takes off pressure is boosted in the cabin of the plane, and the data of the barometric pressure sensor is invalid. If the smart watch determines, after determining that the data of the barometric pressure sensor is invalid, that the GPS function is in the enabled state, the smart watch displays the altitude in the received data of the GPS. In addition, the state identifier of the barometric pressure sensor is updated to 1, to indicate that the data of the barometric pressure sensor is invalid. If the user disables the "Take a plane" mode on the smart watch in the flight process of the plane, the GPS function is disabled. The smart watch detects that the GPS function is disabled, and determines that the data of the barometric pressure sensor is invalid (the state identifier of the barometric pressure sensor is 1), and in this case, the smart watch periodically enables the GPS function based on the preset first time interval. In this way, the smart watch can display the altitude in the received data of the GPS. Subsequently, when the plane that the user takes lands, pressure is no longer boosted in the cabin of the plane, and the smart watch detects that the data of the barometric pressure sensor becomes valid again, the smart watch stops periodically enabling the GPS function based on the preset first time interval, and display the altitude obtained based on the barometric pressure value measured by the barometric pressure sensor.

S305: The electronic device displays the altitude obtained in the first detection manner.

For example, the electronic device displays the current altitude based on the barometric pressure value measured by the barometric pressure sensor.

Figure 6:
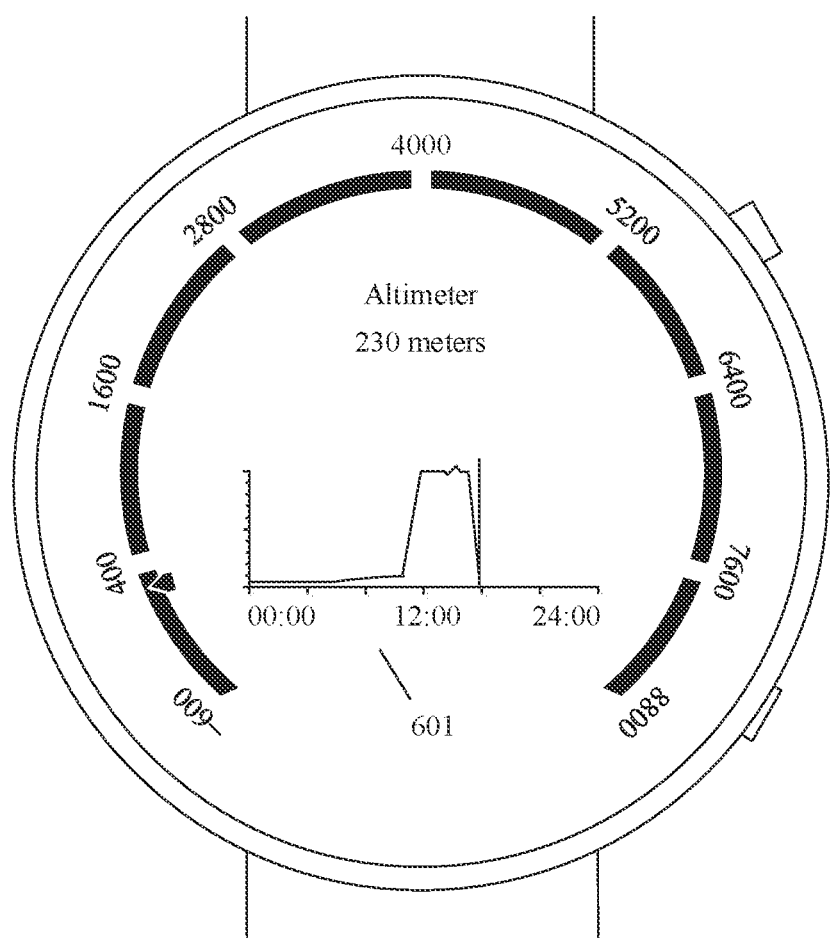
FIG. 6 is a schematic diagram 6 of an example of a display interface of an electronic device according to an embodiment of this application.

For example, after the plane lands, the smart watch displays the altitude obtained based on the barometric pressure value measured by the barometric pressure sensor. As shown in FIG. 6, the smart watch displays a current altitude 230 meters.

Optionally, the smart watch may display an altitude change curve in a period of time. For example, a curve 601 in FIG. 6 is an altitude change curve of the smart watch on the day.

According to the method for measuring a height on a plane provided in this embodiment of this application, generally, the height value displayed by the electronic device is the altitude obtained by using the barometric pressure sensor. When the user takes a plane with the electronic device, the electronic device determines that the data of the barometric pressure sensor is invalid, and the electronic device displays the altitude in the received data of the GNSS. In this way, the electronic device can also display an accurate altitude when the data of the barometric pressure sensor is untrustworthy in a case in which the user takes a plane or in another case.

After the plane that the user takes lands, the electronic device detects that the data of the barometric pressure sensor becomes valid again, and the electronic device displays the altitude obtained by using the barometric pressure sensor. The altitude obtained based on the barometric pressure value measured by the barometric pressure sensor is more accurate than the altitude obtained by receiving the data of the GNSS by the electronic device. In this way, the electronic device can display a more accurate altitude when the user does not take a plane. In addition, in this way, the electronic device may not enable the GNSS function when the user does not take a plane, so that power consumption of the electronic device is reduced.

It may be understood that the method for measuring a height on a plane provided in this embodiment of this application may be further applied to another scenario in which the user wears the electronic device on a transportation tool other than the plane and data of the barometric pressure sensor is invalid. Generally, the electronic device displays the altitude obtained by using the barometric pressure sensor. When determining that the data of the barometric pressure sensor is invalid, the electronic device displays the altitude in the received data of the GNSS. When detecting that the data of the barometric pressure sensor becomes valid again, the electronic device displays the altitude obtained by using the barometric pressure sensor. In this way, the electronic device can display an accurate altitude regardless of whether the data of the barometric pressure sensor is valid.

It can be understood that, to implement the foregoing functions, the electronic device includes a corresponding hardware structure and/or software module for performing each of the functions. A person skilled in the art should be easily aware that, in combination with the examples described in the embodiments disclosed in this specification, units, algorithms, and steps may be implemented by hardware or a combination of hardware and computer software in the embodiments of this application. Whether a function is performed by hardware or hardware driven by computer software depends on particular applications and design constraints of the technical solutions. A person skilled in the art may use different methods to implement the described functions for each particular application, but it should not be considered that the implementation goes beyond the scope of the embodiments of this application.

In the embodiments of this application, the electronic device may be divided into functional modules based on the foregoing method examples. For example, each functional module may be obtained through division based on each corresponding function, or two or more functions may be integrated into one processing module. The integrated module may be implemented in a form of hardware, or may be implemented in a form of a software function module, it should be noted that, in this embodiment of this application, division into the modules is an example, and is merely a logical function division. In an actual implementation, another division manner may be used.

Figure 7:
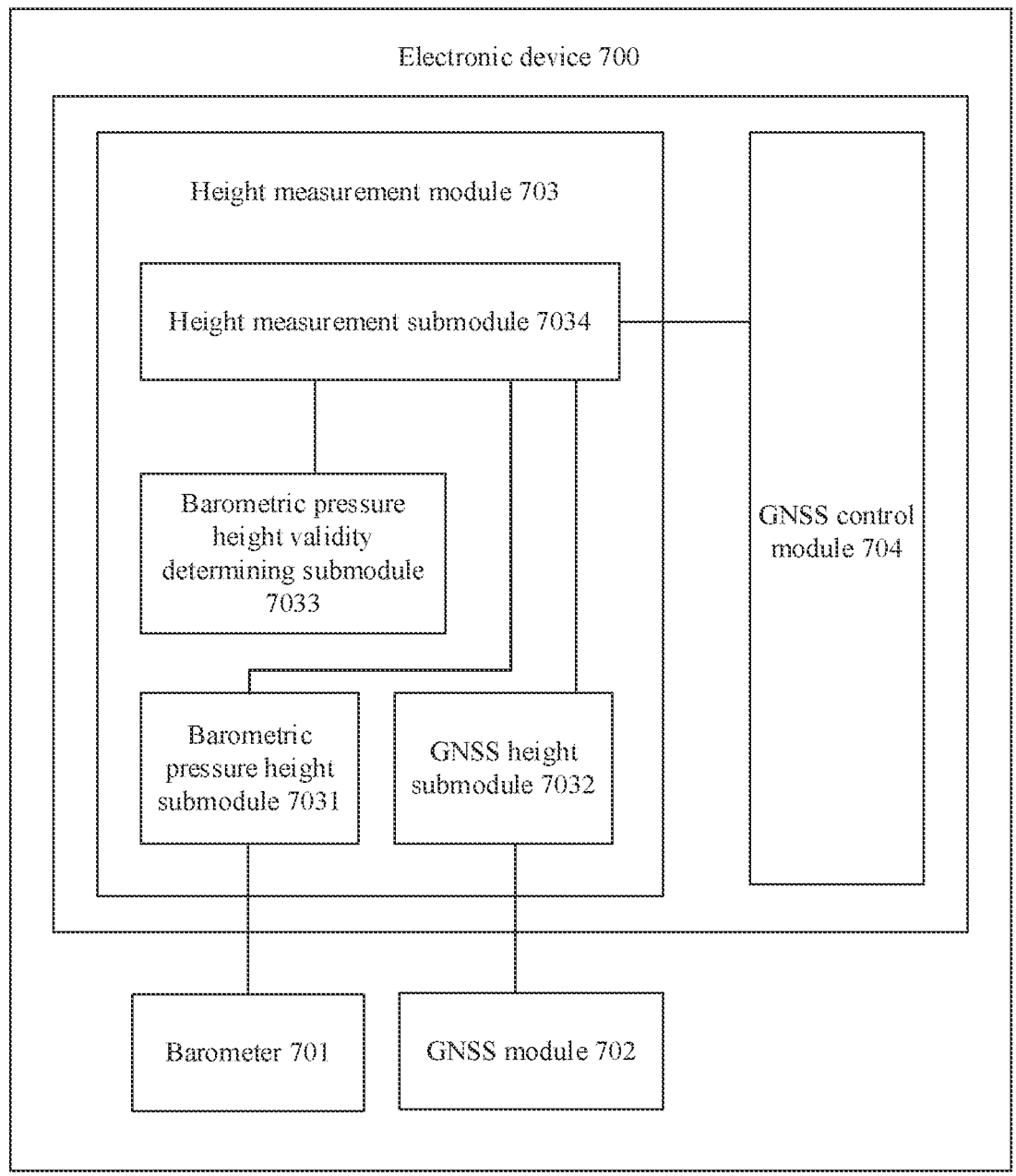
FIG. 7 is a schematic composition diagram 5 of a structure of an electronic device according to an embodiment of this application.
Figure 8A:
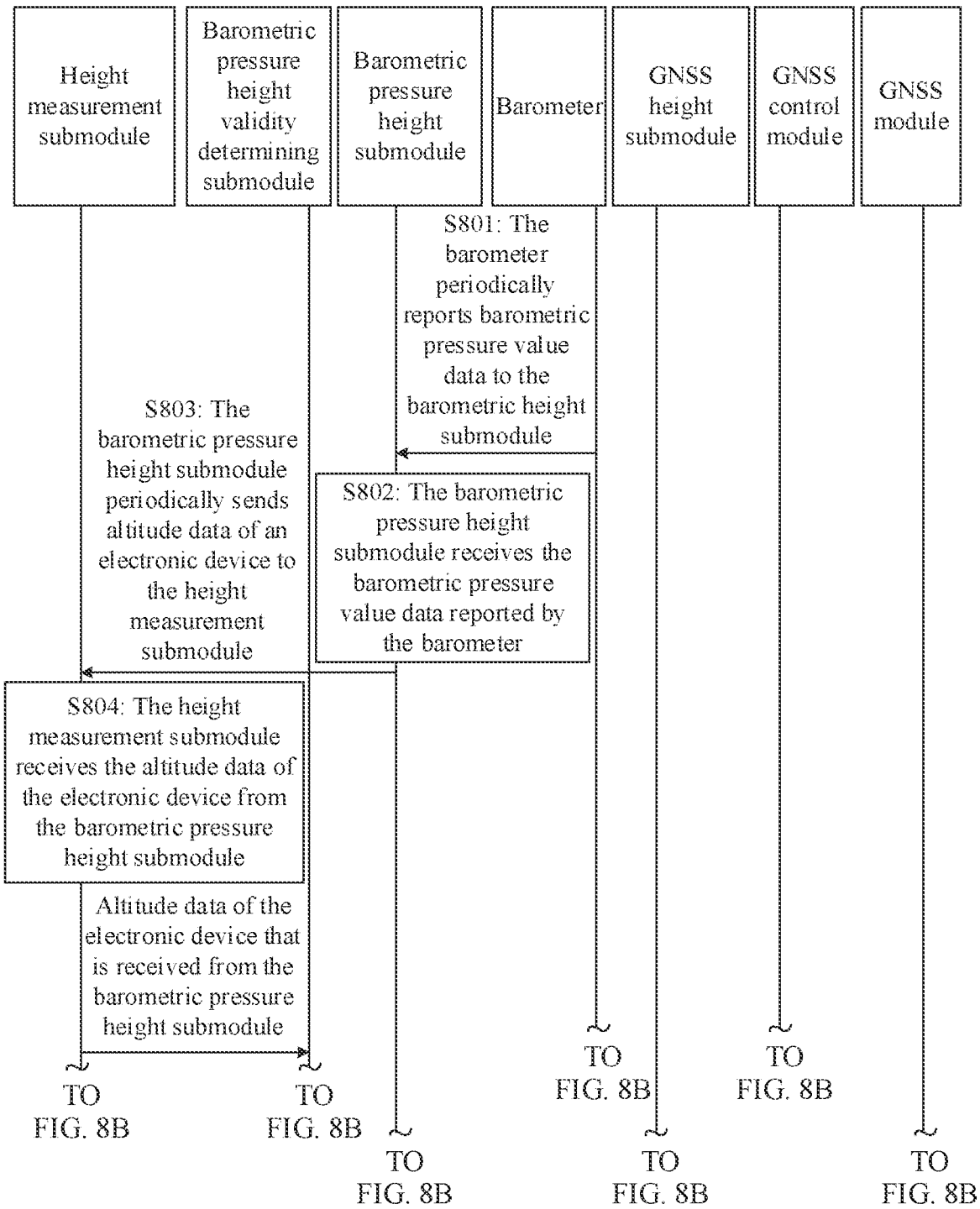
FIG. 8A, FIG. 8B, FIG. 8C, and FIG. 8D are a flowchart 2 of a method for measuring a height on a plane according to an embodiment of this application.
Figure 8B:
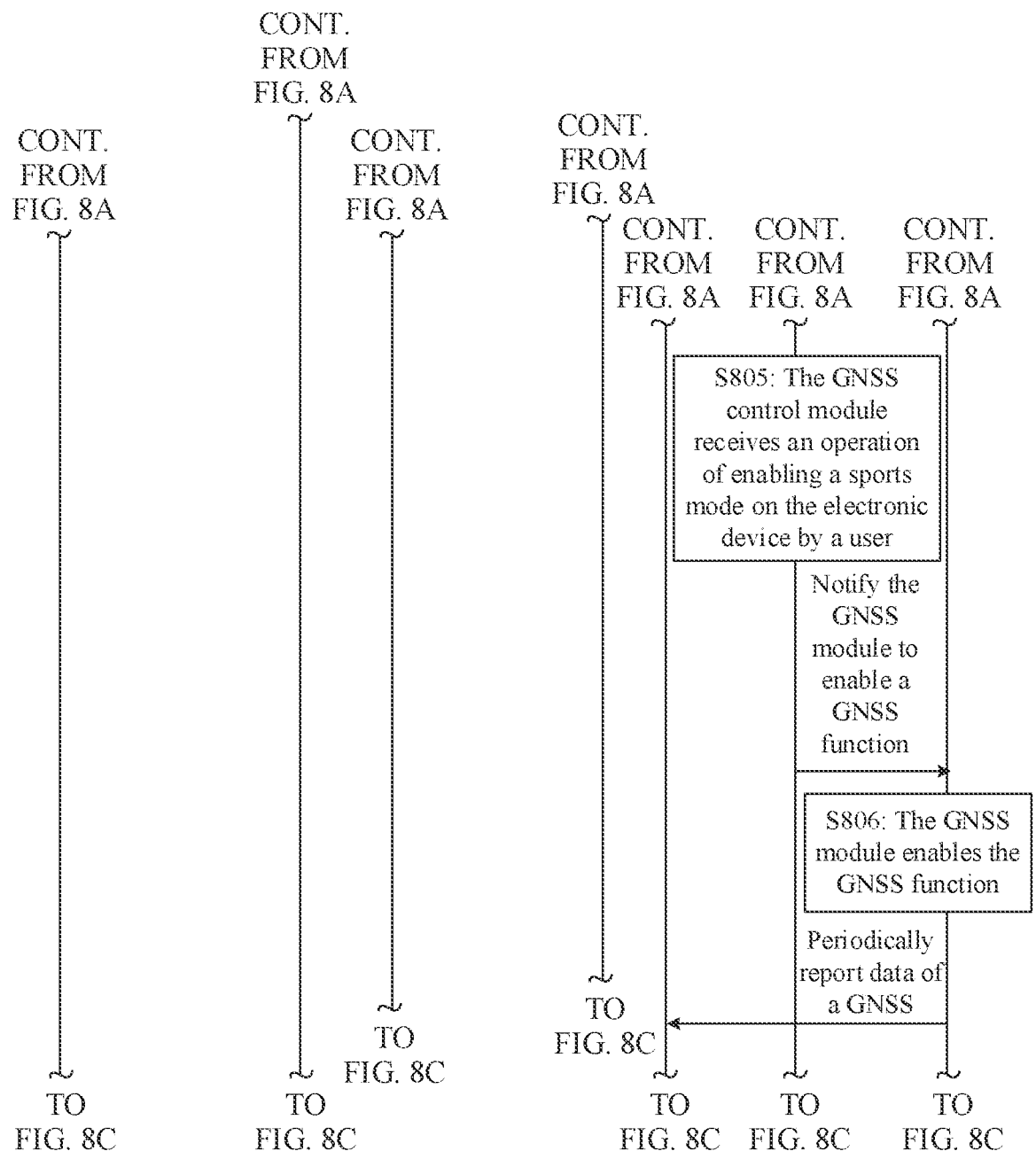
Figure 8C:
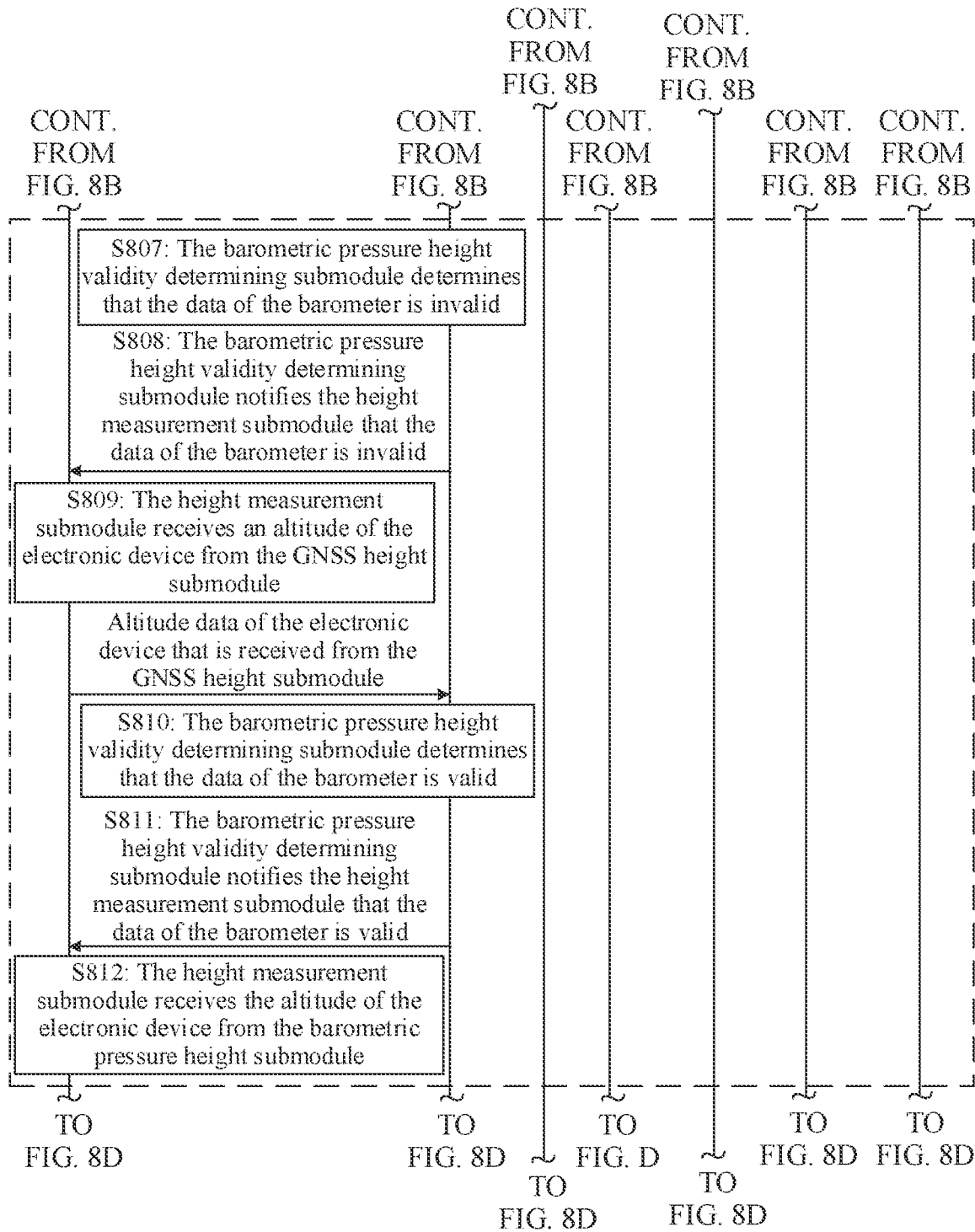
Figure 8D:
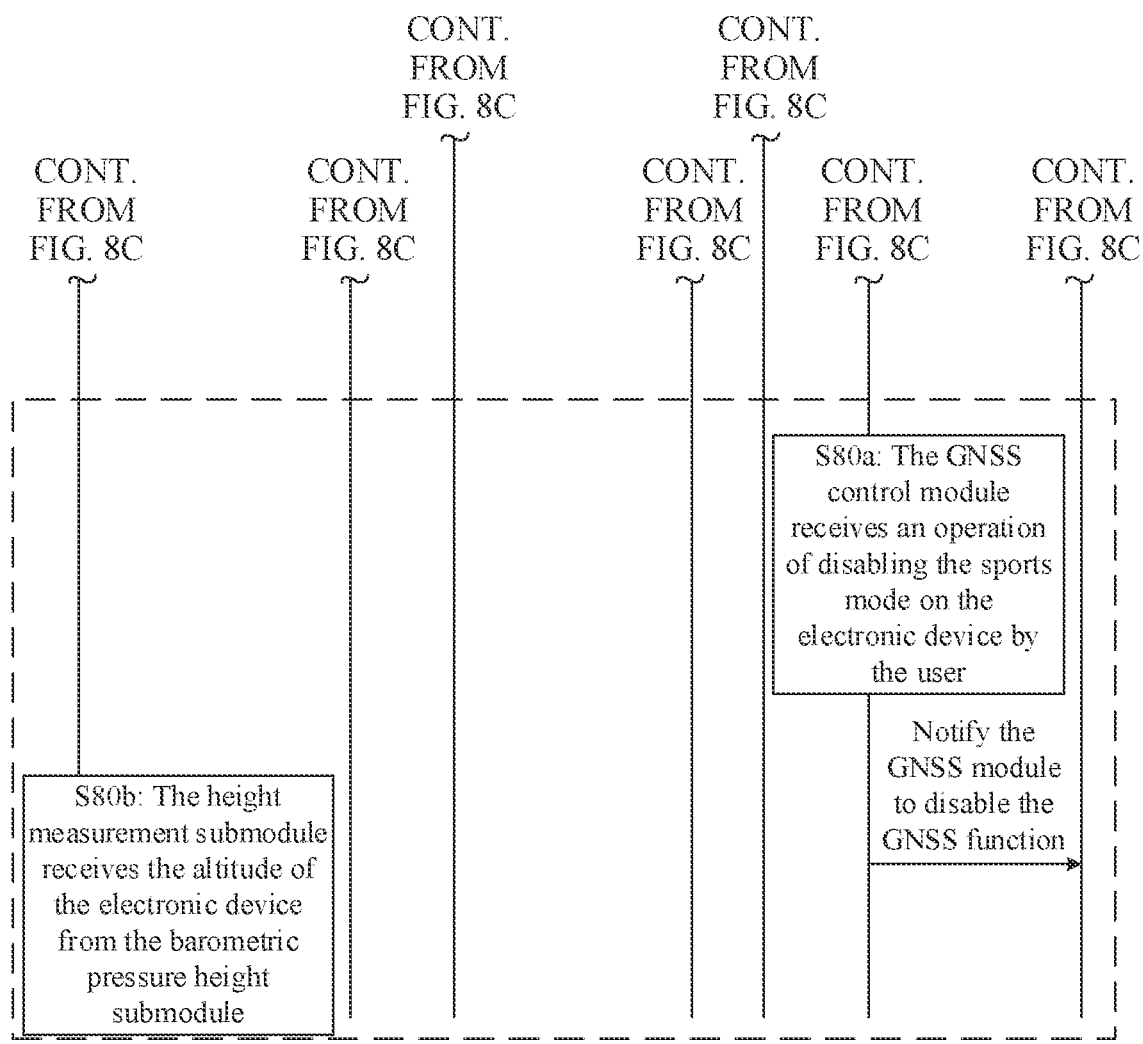

FIG. 7 is a possible schematic diagram of a structure of the electronic device in the foregoing embodiments. The electronic device 700 includes a barometer 701, a GNSS module 702, a height measurement module 703, and a GNSS control module 704.

The barometer 701 is configured to detect a barometric pressure value. For example, the barometer 701 may be the barometric pressure sensor 150A in FIG. 2A.

The GNSS module 702 is configured to receive data of a GNSS. For example, the GNSS module 702 may be the positioning module 160 in FIG. 2A.

The height measurement module 703 is configured to calculate an altitude of the electronic device. The height measurement module 703 includes: a barometric pressure height submodule 7031, configured to calculate the altitude of the electronic device based on the barometric pressure value detected by the barometer 701; a GNSS height submodule 7032, configured to obtain the altitude of the electronic device based on the data of the GNSS; a barometric pressure height validity determining submodule 7033, configured to determine whether the data of the barometer 701 is valid; and a height measurement submodule 7034, configured to obtain the altitude of the electronic device based on the data of the submodules in the height measurement module 703, and further configured to interact with another module of the electronic device as an interface module of the height measurement module 703.

The GNSS control module 704 is configured to control a GNSS function of the electronic device to be enabled or disabled. For example, the GNSS control module 704 may be configured to control, based on an operation of enabling or disabling a sports mode by a user, the GNSS function of the electronic device to be enabled or disabled. For example, if the GNSS control module 704 determines that an operation of enabling an outdoor sports mode such as walking, outdoor running, riding, or mountain climbing by the user is received, or determines that an operation of enabling a "Take a plane" mode in the sports mode by the user is received, the GNSS control module 704 controls the GNSS function of the electronic device to be enabled; or if the GNSS control module 704 determines that an operation of disabling an outdoor sports mode such as walking, outdoor running, riding, or mountain climbing by the user is received, or determines that an operation of disabling a "Take a plane" mode in the sports mode by the user is received, the GNSS control module 704 controls the GNSS function of the electronic device to be disabled. For example, the GNSS control module 704 may be further configured to control, based on an operation of enabling or disabling a positioning function by the user, the GNSS function of the electronic device to be enabled or disabled. Content of controlling the GNSS function to be enabled/disabled is described in detail in the foregoing embodiments, and is not described herein again.

For example, the height measurement module 703 and the GNSS control module 704 may be implemented by the processor 110 in FIG. 2A.

With reference to an interaction procedure between the modules of the electronic device 700, the following describes in detail the method for measuring a height on a plane provided in the embodiments of this application.

Scenario 1: A user enables a GNSS function of an electronic device before a plane takes off. Subsequently, the user takes a plane with the electronic device, and the plane takes off After the plane takes off pressure is boosted in a cabin of the plane, and data of a barometer of the electronic device is invalid.

This embodiment is described by using an example in which the user enables the GNSS function of the electronic device by enabling an outdoor sports mode or a "Take a plane" mode on the electronic device. Certainly, the user may alternatively enable the GNSS function in another manner before the plane takes off. For example, before the plane takes off, the user enables the GNSS function by enabling a positioning function of the electronic device. A specific manner in which the user enables the GNSS function does not affect a function of each module in this embodiment. Descriptions of functions of the modules and descriptions of an interaction procedure between the modules in this embodiment are also applicable to a scenario in which the user enables the GNSS function in another manner.

It should be noted that the sports mode in this embodiment is an outdoor sports mode such as walking, outdoor running, riding, or mountain climbing or a "Take a plane" mode. This is not specifically described in specific descriptions of the embodiments.

As shown in FIG. 8A, FIG. 8B, FIG. 8C, and FIG. 8D, a method for measuring a height on a plane provided in an embodiment of this application may include the following steps.

S801: A barometer periodically reports barometric pressure value data to a barometric pressure height submodule.

For example, the barometer periodically reports the detected barometric pressure value data to the barometric pressure height submodule based on a specified period (for example, 1 second).

S802: The barometric pressure height submodule receives the barometric pressure value data reported by the barometer.

The barometric pressure height submodule receives the barometric pressure value data reported by the barometer, and may calculate an altitude of an electronic device based on the barometric pressure value. The barometric pressure height submodule may send the altitude data of the electronic device to a height measurement submodule, and may also send the altitude data of the electronic device a barometric pressure height validity determining submodule.

S803: The barometric pressure height submodule periodically sends the altitude data of the electronic device to the height measurement submodule.

S804: The height measurement submodule receives the altitude data of the electronic device from the barometric pressure height submodule.

After the height measurement submodule receives the altitude data of the electronic device, the electronic device may display the altitude on a display. For example, when a user does not take a plane, the electronic device displays an interface shown in FIG. 1, and an altitude value of the electronic device is 121 meters.

The height measurement submodule may further send, to the barometric pressure height validity determining submodule, the altitude data of the electronic device that is received from the barometric pressure height submodule.

S805: A GNSS control module receives an operation of enabling a sports mode on the electronic device by the user.

The GNSS control module receives the operation of enabling the sports mode on the electronic device by the user, and notifies, in response to the operation of enabling the sports mode on the electronic device by the user, a GNSS module to enable a GNSS function.

S806: The GNSS module enables the GNSS function.

The GNSS module may enable the GNSS function, and after receiving an operation of disabling the sports mode on the electronic device by the user, the GNSS control module notifies the GNSS module to disable the GNSS function.

When the GNSS function is enabled, the GNSS module may periodically (for example, a reporting period is 1 second) report received data of a GNSS to a GNSS height submodule.

The GNSS height submodule receives the data of the GNSS, and may obtain an altitude of the electronic device based on the data of the GNSS.

S807: The barometric pressure height validity determining submodule determines that the data of the barometer is invalid.

The barometric pressure height validity determining submodule periodically receives the altitude data of the electronic device that is sent by the height measurement submodule (the altitude data of the electronic device is received from the barometric pressure height submodule). If the barometric pressure height validity determining submodule determines, based on the altitude data of the electronic device that is received from the barometric pressure height submodule, that a first preset condition is met, the barometric pressure height validity determining submodule determines that the data of the barometer is invalid. For example, if the barometric pressure height validity determining submodule determines that the altitude data of the electronic device increases by 100 meters within 30 seconds, the barometric pressure height validity determining submodule determines that the data of the barometer is invalid.

For example, the user takes a plane with the electronic device, and the plane takes off. After the plane takes off, pressure is boosted in a cabin of the plane, and the data of the barometer is invalid.

S808: The barometric pressure height validity determining submodule notifies the height measurement submodule that the data of the barometer is invalid.

S809: The height measurement submodule receives the altitude of the electronic device from the GNSS height submodule.

If the height measurement submodule determines, after receiving a notification message that the data of the barometer is invalid, that the GNSS function of the electronic device is enabled, the height measurement submodule receives the altitude of the electronic device from the GNSS height submodule. In this way, the electronic device displays the altitude data in the received data of the GNSS.

For example, the electronic device displays an interface shown in FIG. 4, and an altitude value of the electronic device is 8500 meters.

The height measurement submodule may further send, to the barometric pressure height validity determining submodule, the altitude data of the electronic device that is received from the GNSS height submodule.

In a possible scenario, the plane that the user takes lands, pressure is no longer boosted in the cabin of the plane, and the data of the barometer becomes valid again. The method may further include the following steps.

S810: The barometric pressure height validity determining submodule determines that the data of the barometer is valid.

In an implementation, the barometric pressure height validity determining submodule compares the altitude data of the electronic device that is received from the barometric pressure height submodule and the altitude data of the electronic device that is received from the GNSS height submodule. If the barometric pressure height validity determining submodule determines that an absolute value of a difference between the altitude data of the electronic device that is received from the barometric pressure height submodule and the altitude data of the electronic device that is received from the GNSS height submodule is less than a preset threshold, the barometric pressure height validity determining submodule determines that the data of the barometer is valid.

S811: The barometric pressure height validity determining submodule notifies the height measurement submodule that the data of the barometer is valid.

S812: The height measurement submodule receives the altitude of the electronic device from the barometric pressure height submodule.

The height measurement submodule stops receiving the altitude of the electronic device from the GNSS height submodule, and receives the altitude of the electronic device from the barometric pressure height submodule again. In this way, the electronic device displays the altitude data of the electronic device that is received from the barometric pressure height submodule.

For example, after the plane lands, the electronic device displays an interface shown in FIG. 6, and an altitude value of the electronic device is 230 meters.

In a possible scenario, the user may disable the GNSS function in a flight process of the plane. For example, if the user disables, on a smart watch, the sports mode on the electronic device in the flight process of the plane, disabling the GNSS function may be triggered. The method may further include the following steps.

S80a: The GNSS control module receives an operation of disabling the sports mode on the electronic device by the user.

The GNSS control module receives the operation of disabling the sports mode on the electronic device by the user, and the GNSS control module notifies, in response to the operation of disabling the sports mode on the electronic device by the user, the GNSS module to disable the GNSS function. The GNSS module stops periodically reporting the received data of the GNSS to the GNSS height submodule.

It may be understood that the height measurement submodule is an interface module between the height measurement module and another module, and the GNSS control module may notify, by using the height measurement submodule, the GNSS module to disable the GNSS function. In this case, the height measurement submodule may determine that the GNSS function is disabled.

S80b: The height measurement submodule receives the altitude of the electronic device from the barometric pressure height submodule.

The height measurement submodule stops receiving the altitude of the electronic device from the GNSS height submodule, and receives the altitude of the electronic device from the barometric pressure height submodule again. In this way, the electronic device displays the altitude data of the electronic device that is received from the barometric pressure height submodule.

According to the method for measuring a height on a plane provided in this embodiment of this application, generally, the height value displayed by the electronic device is the altitude obtained by using the barometric pressure sensor. The user may enable the GNSS function of the electronic device. When the user takes a plane with the electronic device, the electronic device determines that the data of the barometric pressure sensor is invalid, and the electronic device displays the altitude in the received data of the GNSS. In this way, the electronic device can also display an accurate altitude when the data of the barometric pressure sensor is untrustworthy in a case in which the user takes a plane or in another case.

After the plane that the user takes lands, the electronic device detects that the data of the barometric pressure sensor becomes valid again, and the electronic device displays the altitude obtained by using the barometric pressure sensor. The altitude obtained based on the barometric pressure value measured by the barometric pressure sensor is more accurate than the altitude obtained by receiving the data of the GNSS by the electronic device. In this way, the electronic device can display a more accurate altitude when the user does not take a plane.

If the user disables the GNSS function in the flight process of the plane, the electronic device displays the altitude obtained by using the barometric pressure sensor.

Scenario 2: A user takes a plane with an electronic device, and the plane takes off After the plane takes off, pressure is boosted in a cabin of the plane, and data of a barometer of the electronic device is invalid. The user does not enable a GNSS function of the electronic device.

Figure 9A:
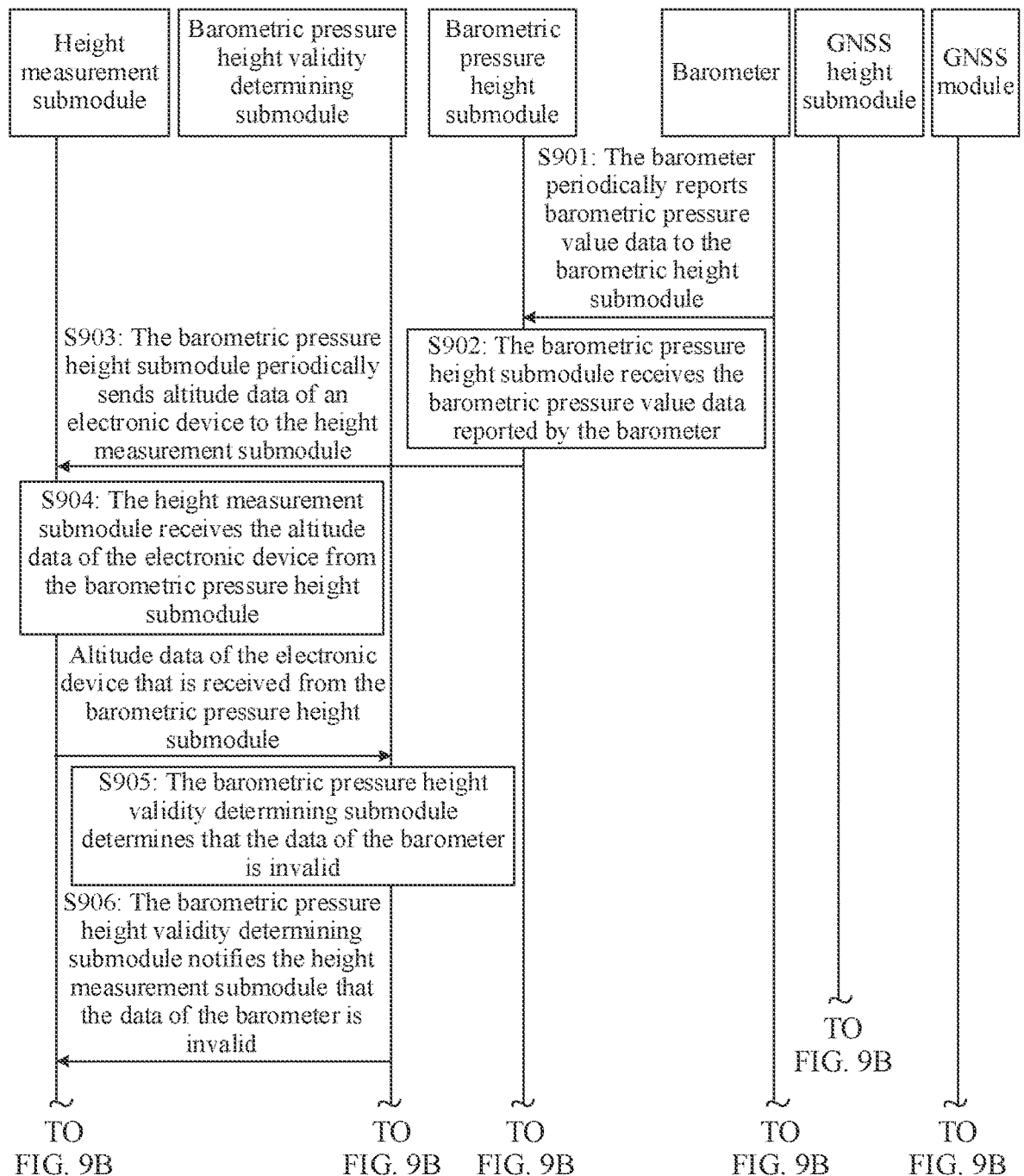
FIG. 9A and FIG. 9B are a flowchart 3 of a method for measuring a height on a plane according to an embodiment of this application.
Figure 9B:
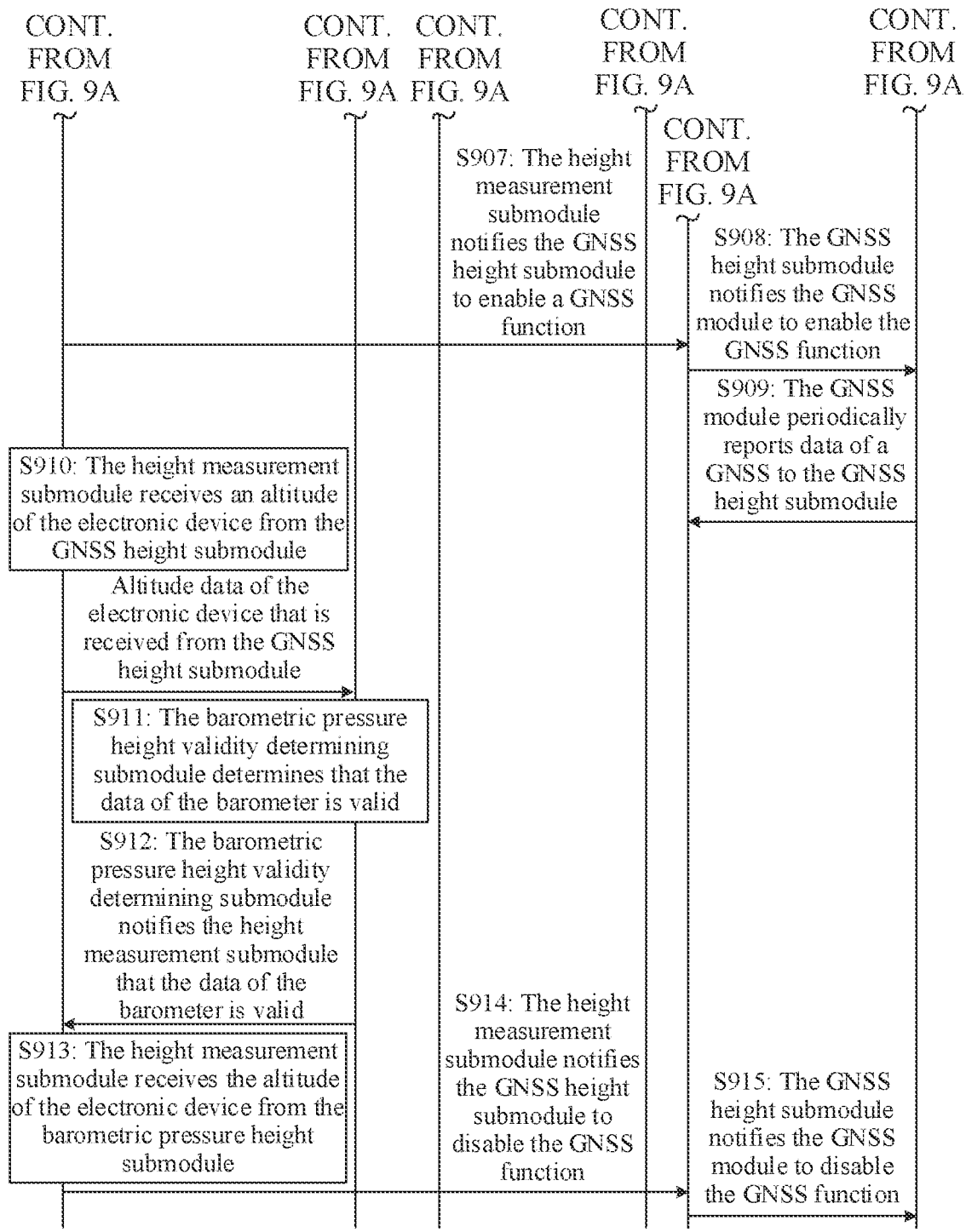

As shown in FIG. 9A and FIG. 9B, a method for measuring a height on a plane provided in an embodiment of this application may include the following steps.

S901: A barometer periodically reports barometric pressure value data to a barometric pressure height submodule.

S902: The barometric pressure height submodule receives the barometric pressure value data reported by the barometer.

S903: The barometric pressure height submodule periodically sends altitude data of an electronic device to a height measurement submodule.

S904: The height measurement submodule receives the altitude data of the electronic device from the barometric pressure height submodule.

For detailed descriptions of S901 to S904, refer to S801 to S804. Details are not described herein again.

S905: The barometric pressure height validity determining submodule determines that the data of the barometer is invalid.

For detailed descriptions of S905, refer to S807. Details are not described herein again.

S906: The barometric pressure height validity determining submodule notifies the height measurement submodule that the data of the barometer is invalid.

For detailed descriptions of S906, refer to S808. Details are not described herein again.

S907: The height measurement submodule notifies a GNSS height submodule to enable a GNSS function.

The height measurement submodule determines that the electronic device no longer displays the altitude data of the electronic device that is received from the barometric pressure height submodule, and notifies the GNSS height submodule to enable the GNSS function.

In an implementation, the height measurement submodule continues to receive the altitude data of the electronic device from the barometric pressure height submodule. In this case, the height measurement submodule may determine, based on the altitude data of the electronic device that is received from the barometric pressure height submodule, whether the data of the barometer becomes valid again.

S908: The GNSS height submodule notifies a GNSS module to enable the GNSS function.

The GNSS height submodule notifies the GNSS module to enable the GNSS function. After receiving the notification of enabling the GNSS function from the GNSS height submodule, the GNSS module enables the GNSS function, and receives data of a GNSS.

In an implementation, the GNSS height submodule periodically enables the GNSS function based on a preset first time interval. In each period, the GNSS function is disabled after an enabled state of the GNSS function lasts for preset duration. The GNSS module periodically enables the GNSS function based on the preset first time interval. In each period, after the data of the GNSS has been received for preset duration, the GNSS module stops receiving the data of the GNSS.

S909: The GNSS module periodically reports the data of the GNSS to the GNSS height submodule.

When the GNSS function is enabled, the GNSS module reports the data of the GNSS to the GNSS height submodule. The GNSS height submodule receives the data of the GNSS, and may obtain an altitude of the electronic device based on the data of the GNSS.

S910: The height measurement submodule receives the altitude of the electronic device from the GNSS height submodule.

The height measurement submodule receives the altitude of the electronic device from the GNSS height submodule. In this way, the electronic device displays the altitude data in the received data of the GNSS.

For example, the electronic device displays an interface shown in FIG. 4, and an altitude value of the electronic device is 8500 meters.

The height measurement submodule may further send, to the barometric pressure height validity determining submodule, the altitude of the electronic device that is received from the GNSS height submodule.

S911: The barometric pressure height validity determining submodule determines that the data of the barometer is valid.

For example, a plane that a user takes lands, pressure is no longer boosted in a cabin of the plane, the data of the barometer becomes valid again, and the barometric pressure height validity determining submodule determines that the data of the barometer is valid.

In an implementation, the barometric pressure height validity determining submodule compares the altitude data of the electronic device that is received from the barometric pressure height submodule and the altitude data of the electronic device that is received from the GNSS height submodule. If the barometric pressure height validity determining submodule determines that an absolute value of a difference between the altitude data of the electronic device that is received from the barometric pressure height submodule and the altitude data of the electronic device that is received from the GNSS height submodule is less than a preset threshold, the barometric pressure height validity determining submodule determines that the data of the barometer is valid.

S912: The barometric pressure height validity determining submodule notifies the height measurement submodule that the data of the barometer is valid.

S913: The height measurement submodule receives the altitude of the electronic device from the barometric pressure height submodule.

The height measurement submodule stops receiving the altitude of the electronic device from the GNSS height submodule, and receives the altitude of the electronic device from the barometric pressure height submodule again. In this way, the electronic device displays the altitude data of the electronic device that is received from the barometric pressure height submodule. For example, after the plane lands, the electronic device displays an interface shown in FIG. 6, and an altitude value of the electronic device is 230 meters.

S914: The height measurement submodule notifies the GNSS height submodule to disable the GNSS function.

The height measurement submodule determines that the electronic device no longer displays the altitude data of the electronic device that is received from the GNSS height submodule, and notifies the GNSS height submodule, to disable the GNSS function.

S915: The GNSS height submodule notifies the GNSS module to disable the GNSS function.

The GNSS height submodule notifies the GNSS module to disable the GNSS function. After receiving the notification of disabling the GNSS function from the GNSS height submodule, the GNSS module disables the GNSS function, and no longer receives the data of the GNSS.

In an implementation, the GNSS height submodule determines to stop periodically enabling the GNSS function based on the preset first time interval. The GNSS height submodule notifies the GNSS module to stop periodically enabling the GNSS function based on the preset first time interval. After receiving the notification from the GNSS height submodule, the GNSS module stops periodically receiving the data of the GNSS based on the preset first time interval.

According to the method for measuring a height on a plane provided in this embodiment of this application, generally, the height value displayed by the electronic device is the altitude obtained by using the barometric pressure sensor. When the user takes a plane with the electronic device, the electronic device determines that the data of the barometric pressure sensor is invalid, and the electronic device may enable the GNSS function, and display the altitude in the received data of the GNSS. In this way, the electronic device can also display an accurate altitude when the data of the barometric pressure sensor is untrustworthy in a case is which the user takes a plane or in another case. In addition, the electronic device may periodically and intermittently enable the GNSS function, so that power consumption of the electronic device can be reduced.

After the plane that the user takes lands, the electronic device detects that the data of the barometric pressure sensor becomes valid again, and the electronic device displays the altitude obtained by using the barometric pressure sensor. The altitude obtained based on the barometric pressure value measured by the barometric pressure sensor is more accurate than the altitude obtained by receiving the data of the GNSS by the electronic device. In this way, the electronic device can display a more accurate altitude when the user does not take a plane. In addition, in this way, the electronic device may not enable the GNSS function when the user does not take a plane, so that power consumption of the electronic device is reduced.

Figure 10:
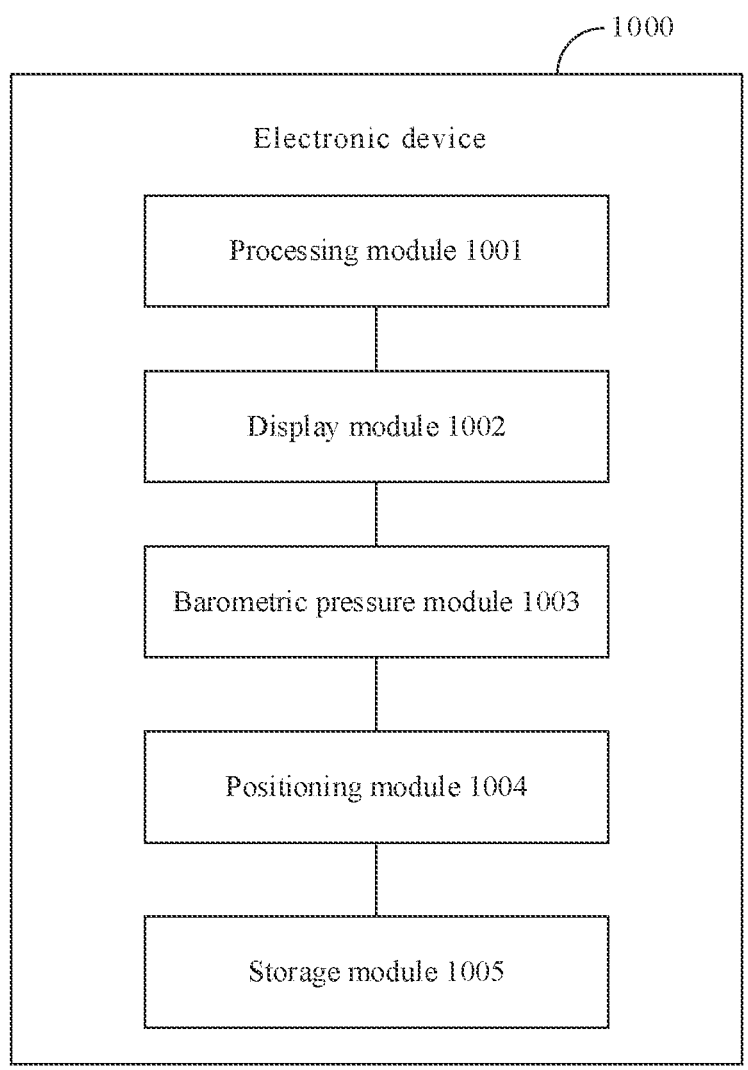
FIG. 10 is a schematic composition diagram 6 of a structure of an electronic device according to an embodiment of this application.

When an integrated unit is used, FIG. 10 is a possible schematic diagram of a structure of the electronic device in the foregoing embodiments. The electronic device 1000 includes a processing module 1001, a display module 1002, a barometric pressure module 1003, a positioning module 1004, and a storage module 1005.

The processing module 1001 is configured to control and manage an action of the electronic device 1000. For example, the processing module 1001 may be configured to perform the processing steps of S302 and S304 in FIG. 3 and/or another process of the technology described in this specification.

The display module 1002 is configured to display an interface of the electronic device. For example, the display module 1002 may be configured to display an altitude of the electronic device, and may be further configured to: display a setting interface for enabling and disabling a sports mode of the electronic device, and display a setting interface for enabling and disabling a positioning function. For example, the display module 1002 may be configured to perform the processing steps of S301, S303, and S305 in FIG. 3 and/or another process of the technology described in this specification.

The barometric pressure module 1003 is configured to detect barometric pressure of an environment in which the electronic device 1000 is located.

The positioning module 1004 is configured to position the electronic device 1000. For example, the positioning module 1004 may be configured to receive data of a GNSS, The storage module 1005 is configured to store program code and data of the electronic device 1000. For example, the storage module 1005 may be configured to store a state identifier of a barometric pressure sensor.

Certainly, units and modules in the electronic device 1000 include but are not limited to the processing module 1001, the display module 1002, the barometric pressure module 1003, the positioning module 1004, and the storage module 1005. For example, the electronic device 1000 may further include a power module.

The processing unit 1001 may be a processor or a controller, for example, may be a central processing unit (central processing unit, CPU), a digital signal processor (digital signal processor, DSP), or an application-specific integrated circuit (application-specific integrated circuit, ASIC), a field programmable gate array (field programmable gate array, FPGA) or another programmable logic component, a transistor logic component, a hardware component, or any combination thereof. The processor may include an application processor and a baseband processor. The processing module may implement or execute various example logical blocks, modules, and circuits described with reference to content disclosed in this application. The processor may be a combination of processors implementing a computing function, for example, a combination of one or more microprocessors, or a combination of the DSP and a microprocessor. The display module 1002 may be a display. The barometric pressure module 1003 may be a barometric pressure sensor. The storage module 1005 may be a memory.

For example, the processing module 1001 is a processor (the processor 110 shown in FIG. 2A), the display module 1002 is a display (the display 130 shown in FIG. 2A, where the display 130 may be a touchscreen, and a display panel and a touch panel may be integrated into the touchscreen), the barometric pressure module 1003 is a barometric pressure sensor (the barometric pressure sensor 150A shown in FIG. 2A), the positioning module 1004 may be the positioning module 160 shown in FIG. 2A, and the storage module 1005 may be a memory (the memory 120 shown in FIG. 2A). The processor, the memory, and the like may be coupled together, for example, connected by using a bus.

An embodiment of this application further provides a computer storage medium. The computer storage medium stores computer program code, and when the processor executes the computer program code, the electronic device performs related method steps in FIG. 3 to implement the method in the foregoing embodiments.

An embodiment of this application further provides a computer program product. When the computer program product runs on a computer, the computer performs the related method steps in FIG. 3 to implement the method in the foregoing embodiment.

The electronic device 1000, the computer storage medium, and the computer program product provided in the embodiments of this application each are configured to perform the corresponding method provided above. Therefore, for beneficial effects that can be achieved by the electronic device 1000, the computer storage medium, and the computer program product, refer to the beneficial effects in the corresponding method provided above. Details are not described herein again.

The foregoing descriptions about the implementations allow a person skilled in the art to clearly understand that, for the purpose of convenient and brief description, division into only the foregoing function modules is used as an example for description. In actual application, the foregoing functions can be allocated to different function modules for implementation as required. In other words, an inner structure of an apparatus is divided into different function modules to implement all or some of the functions described above.

In the several embodiments provided in this application, it should be understood that the disclosed apparatuses and methods may be implemented in other manners. For example, the described apparatus embodiments are merely examples. For example, division into the modules or units is merely logical function division, and may be other division in an actual implementation. For example, a plurality of units or components may be combined or may be integrated into another apparatus, or some features may be ignored or not performed. In addition, the displayed or discussed mutual couplings or direct couplings or communications connections may be implemented through some interfaces. The indirect couplings or communications connections between the apparatuses or units may be implemented in electronic, mechanical, or another form.

The units described as separate components may or may not be physically separate, and components displayed as units may be one or more physical units, that is, may be located in one place, or may be distributed on a plurality of different places. A part or all of the units may be selected based on actual requirements to achieve the objectives of the solutions of the embodiments.

In addition, function units in the embodiments of this application may be integrated into one processing unit, or each of the units may exist alone physically, or two or more units may be integrated into one unit. The integrated unit may be implemented in a form of hardware, or may be implemented in a form of a software function unit.

When the integrated unit is implemented in a form of a software function unit and sold or used as an independent product, the integrated unit may be stored in a readable storage medium. Based on such an understanding, the technical solutions of the embodiments of this application essentially, or the part contributing to the conventional technology, or all or some of the technical solutions may be implemented in a form of a software product. The software product is stored in a storage medium and includes several instructions for instructing a device (which may be a single-chip microcomputer, a chip, or the like) or a processor (processor) to perform all or some of the steps of the methods in the embodiments of this application. The foregoing storage medium includes any medium that can store program code, for example, a USB flash drive, a removable hard disk, a ROM, a RAM, a magnetic disk, or an optical disc.

The foregoing description is merely a specific implementation of this application, but is not intended to limit the protection scope of this application. Any variation or replacement within the technical scope disclosed in this application shall fall within the protection scope of this application. Therefore, the protection scope of this application shall be subject to the protection scope of the claims.

What is claimed is:

1. A method, comprising:
obtaining a first altitude of an electronic device in a first detection manner;
displaying the first altitude;
periodically enabling a second detection manner based on a first preset time interval;
obtaining a second altitude of the electronic device in the second detection manner;
periodically comparing, based on the first preset time interval, the first altitude obtained by the first detection manner to the second altitude obtained by the second detection manner M times, wherein M is an integer greater than 1;
responsive to an absolute value of a difference between the first altitude and the second altitude being less than a preset threshold M consecutive times, displaying the first altitude and stopping periodically enabling the second detection manner; and
responsive to the absolute value of the difference between the first altitude and the second altitude being greater than the preset threshold M consecutive times, displaying the second altitude in place of the first altitude.

2. The method of claim 1, wherein the absolute value of the difference between the first altitude and the second altitude being greater than the preset threshold M consecutive times indicates that data obtained in the first detection manner is invalid.

3. The method of claim 2, wherein the data is invalid when the first altitude is greater than a preset first height threshold within a first preset duration.

4. The method of claim 1, further comprising displaying the first altitude when a switching condition is met.

5. The method of claim 4, wherein the switching condition comprises detecting an operation of disabling the second detection manner by a user.

6. The method of claim 1, wherein the first detection manner comprises detecting the first altitude using a barometric pressure sensor, and wherein the second detection manner comprises:
receiving altitude data of a global navigation satellite system (GNSS); and
obtaining the second altitude using the altitude data.

7. The method of claim 6, wherein before displaying the second altitude, the method further comprises enabling a GNSS function of the electronic device.

8. An electronic device comprising:
a memory configured to store instructions; and
one or more processors coupled to the memory, wherein when executed by the one or more processors, the instructions cause the electronic device to:
obtain a first altitude of the electronic device in a first detection manner;
display the first altitude;
periodically enable a second detection manner based on a first preset time interval;
obtain a second altitude of the electronic device in the second detection manner;
periodically compare, based on the first preset time interval, the first altitude obtained by the first detection manner to the second altitude obtained by the second detection manner M times, wherein M is an integer greater than 1;

responsive to an absolute value of a difference between the first altitude and the second altitude being less than a preset threshold M consecutive times, display the first altitude and stop periodically enabling the second detection manner; and responsive to the absolute value of the difference between the first altitude and the second altitude being greater than the preset threshold M consecutive times, display the second altitude in place of the first altitude.

9. The electronic device of claim 8, wherein the absolute value of the difference between the first altitude and the second altitude being greater than the preset threshold M consecutive times indicates that data obtained in the first detection manner is invalid.

10. The electronic device of claim 9, wherein the data is invalid when the first altitude is greater than a preset first height threshold within a first preset duration.

11. The electronic device of claim 8, wherein when executed by the one or more processors, the instructions further cause the electronic device to display the first altitude when a switching condition is met.

12. The electronic device of claim 11, wherein the switching condition comprises detecting an operation of disabling the second detection manner by a user.

13. The electronic device of claim 8, wherein the first detection manner comprises detecting the first altitude using a barometric pressure sensor, and wherein the second detection manner comprises:

receiving altitude data of a global navigation satellite system (GNSS); and obtaining the second altitude using the altitude data.

14. The electronic device of claim 13, wherein before displaying the second altitude, the instructions further cause the electronic device to enable a GNSS function of the electronic device.

15. A computer program product comprising computer-executable instructions that are stored on a non-transitory computer readable storage medium and that, when executed by one or more processors, cause an electronic device to:

obtain a first altitude of the electronic device in a first detection manner;

display the first altitude;

periodically enable a second detection manner based on a first preset time interval;

obtain a second altitude of the electronic device in the second detection manner;

periodically compare, based on the first preset time interval, the first altitude obtained by the first detection manner to the second altitude obtained by the second detection manner M times, wherein M is an integer greater than 1;

responsive to an absolute value of a difference between the first altitude and the second altitude being less than a preset threshold M consecutive times, display the first altitude and stop periodically enabling the second detection manner; and responsive to the absolute value of the difference between the first altitude and the second altitude being greater than the preset threshold M consecutive times, display the second altitude in place of the first altitude.

16. The computer program product of claim 15, wherein the absolute value of the difference between the first altitude and the second altitude being greater than the preset threshold M consecutive times indicates that data obtained in the first detection manner is invalid.

17. The computer program product of claim 15, wherein the instructions further cause the electronic device to display the first altitude when a switching condition is met.

18. The computer program product of claim 17, wherein the switching condition comprises detecting an operation of disabling the second detection manner by a user.

19. The computer program product of claim 15, wherein the first detection manner comprises detecting the first altitude using a barometric pressure sensor, and wherein the second detection manner comprises:

receiving altitude data of a global navigation satellite system (GNSS); and obtaining the second altitude using the altitude data.

20. The computer program product of claim 19, wherein before displaying the second altitude, the instructions further cause the electronic device to enable a GNSS function of the electronic device.

* * * * *